United States Patent
Banks et al.

(10) Patent No.: US 6,603,494 B1
(45) Date of Patent: Aug. 5, 2003

(54) MULTIPLE MODALITY INTERFACE FOR IMAGING SYSTEMS INCLUDING REMOTE SERVICES OVER A NETWORK

(75) Inventors: Seth Richard Banks, Milwaukee, WI (US); Linda Marie Kohli, Waukesha, WI (US); David Alan Littlejohn, Wales, WI (US); Aaron Joseph Schmidt, Wales, WI (US); Thomas Matthew Hanson, Waukesha, WI (US); Elizabeth A. Kuhn, Wauwatosa, WI (US); Kim Marie Ruchti, Brookfield, WI (US); William Murray Stovel, III, Menomonee Falls, WI (US); James Kenneth Cavanaugh, Chesterton, IN (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/473,217

(22) Filed: Dec. 27, 1999

Related U.S. Application Data

(63) Continuation-in-part of application No. 09/200,056, filed on Nov. 25, 1998.

(51) Int. Cl.⁷ .............................. G09G 5/08; A61B 5/05
(52) U.S. Cl. ...................... 345/807; 345/734; 345/740; 345/763; 600/410
(58) Field of Search ................................. 345/846, 854, 345/856, 733, 740, 800, 734–739, 760, 763, 853, 855, 772, 838, 839, 807; 600/407

(56) References Cited

U.S. PATENT DOCUMENTS

| | | | | |
|---|---|---|---|---|
| 4,763,356 A | * | 8/1988 | Day et al. ................. | 178/18.01 |
| 5,079,723 A | * | 1/1992 | Herceg et al. .............. | 340/747 |
| 5,452,416 A | * | 9/1995 | Hilton et al. ................ | 345/424 |
| 5,469,353 A | * | 11/1995 | Pinsky et al. ............... | 382/131 |
| 5,675,744 A | * | 10/1997 | Tsujii ............................ | 705/2 |
| 5,722,420 A | * | 3/1998 | Lee ................................ | 482/4 |
| 5,749,834 A | * | 5/1998 | Hushek ....................... | 324/309 |
| 5,850,221 A | * | 12/1998 | Macrae et al. .............. | 345/846 |
| 5,974,389 A | * | 10/1999 | Clark et al. .................... | 705/3 |
| 6,031,528 A | * | 2/2000 | Langfahl, Jr. ................ | 345/734 |
| 6,246,783 B1 | * | 6/2001 | Avinash ....................... | 382/128 |
| 6,330,005 B1 | * | 12/2001 | Tonelli et al. ............... | 345/734 |
| 6,337,748 B1 | * | 1/2002 | Murata et al. ............... | 358/1.4 |
| 6,353,445 B1 | * | 3/2002 | Babula et al. .............. | 345/733 |

\* cited by examiner

*Primary Examiner*—Kristine Kincaid
*Assistant Examiner*—Thomas J Joseph
(74) *Attorney, Agent, or Firm*—Quarles & Brady, LLP; Carl Horton

(57) ABSTRACT

An imaging system coupled to a network, the network coupling imaging devices of at least first and second different imaging modalities, each modality including functions which are common to each of the first and second modalities, includes an imaging device, a network coupling the imaging device to a remote facility, an interface associated with the imaging device, and a pointing device for moving a pointer icon about the display and for selecting displayed icons. The network provides the imaging device with remote services from the remote facility. The interface includes a display and a programmed data processor for providing a uniform interface image on the display despite the specific modality. The uniform interface image includes a function navigation space including function icons corresponding to procedures which are common to both the first and second imaging modalities and a workspace adjacent the function navigation space for displaying, analyzing and manipulating images of a type consistent with the specific modality. When an icon is selected, the processor correlates the selected icon with a corresponding command and executes the command.

17 Claims, 10 Drawing Sheets

MULTIPLE MODALITY INTERFACE FOR IMAGING SYSTEMS INCLUDING REMOTE SERVICES OVER A NETWORK

CROSS-REFERENCE TO RELATED APPLICATION

This application is a continuation-in-part (CIP) of U.S. patent application Ser. No. 09/200,056, entitled "Multiple Modality Interface For Imaging Systems" by Seth Richard Banks et al. filed on Nov. 15, 1998.

BACKGROUND OF THE INVENTION

The present invention relates generally to the field of medical diagnostic systems, such as imaging systems. More particularly, the invention relates to a system which can be used to interface with any of several different imaging system types.

Traditionally medical facilities have concentrated their efforts on providing the best possible medical services to patients. One area in which the quality of medical services has progressed extremely quickly is in the medical imaging disciplines or modalities which include radiography, fluoroscopy, angiography, magnetic resonance (MR) imaging, ultrasound, nuclear medicine (NM) and computer tomography (CT).

While each of the separate imaging modalities can be used to generate medical images, the medical imaging industry has recognized that each modality is particularly suited for certain imaging techniques and that some modalities are better suited than others for observing specific anatomical phenomenon. For this reason, many medical facilities have acquired a plurality of imaging systems, each of which facilitates a different one of the imaging modalities. This is particularly true in large medical facilities which may have several imaging systems for performing each of the imaging modalities (i.e. several MR systems, several CT systems, etc.). Having several imaging systems each capable of facilitating a different one of the imaging modalities enables a physician to select the best imaging modality for a particular imaging task and therefore increases the usefulness of a resulting image for achieving the particular task. In fact, many medical facilities compete for patients based on the abilities of their medical imaging departments. This imaging department competition places pressure on each medical facility to maintain state of the art imaging departments.

While imaging system quality has increased appreciably, the costs associated with maintaining a state of the art imaging department have also increased appreciably. Unfortunately, despite increased costs associated with providing a state of the art imaging department, recently there has been mounting pressure on many medical facilities to reduce medical costs. For this reasons imaging departments are always looking for ways to decrease department costs while maintaining the highest possible service quality.

In addition to imaging hardware and software costs which are substantial, another expensive component to any successful medical imaging department is imaging personnel which includes radiologists and technologists. A radiologist is a trained physician who specializes in radiology disciplines and typically in other imaging modalities. Technologists are supervised by the radiologists and perform most of the setup, imaging, filming and archiving of images.

Basic training for a technologist in the imaging disciplines typically includes two years of on the job apprenticeship which focuses on the human anatomy and physiology, imaging equipment theory and operation and imaging procedures. In addition to basic training, many technologists obtain additional training in imaging specialties such as ultrasound, NM and radiation therapy. Training in each specialty typically takes about an additional year per specialty. In addition, some technologists obtain further training in sub-specialties such as computer tomography CT, MR and angiography, each of which requires further on the job training. After a successfully completed apprenticeship a technologist performs procedures under the direction of a radiologist.

Because of the differences in the imaging modalities, many medical facilities are staffed with a plurality of technologists, at least one technologist for each imaging modality practiced at the facility. Thus, in some cases a facility may include at lease seven technologists, at least one technologist for each possible modality. While necessary to have a trained technologist in each imaging modality practiced at a facility, such staffing requirements are extremely expensive.

One solution to the excessive technologist staffing problem has been to train technologists in more than a single imaging modality. For example, one technologist may be trained in both NM and CT while another may be trained in fluoroscopy and radiography.

Another solution to the excessive technologist staffing problem has been for medical facilities to share technologists. Thus, for example, a CT technologist may divide her time between three separate medical facilities, every third day spent at a different one of the three facilities.

While both of these solutions reduce costs associated with technologist staffing, each of the solutions is hampered by the current state of imaging systems and the way in which technologists are forced to interact with such systems and system information. An exemplary MR imaging session is instructive in understanding the difficulties associated with training a technologist in more than a single imaging modality.

A typical MR imaging session comprises several different steps including scheduling, analyzing patient information, patient preparation and handling, acquiring image data, displaying images, advanced processing of image data, filming display images, archiving display images, logging completed acquisitions and interpretation and reporting. Each of the different steps often requires a technologist to interact with one or several different department tools. For example, during scheduling a technologist typically uses a scheduling clipboard (i.e. paper on a clipboard) or the like to schedule imaging sessions during the course of a day. A scheduling table appears on the board which typically identifies time, patient, the type of exam required (e.g. C-spine, brain, head, etc.), status, identification number, etc.

As an alternative to a hardcopy clipboard, some facilities now have automated scheduling tools whereby a scheduling computer is used to generate a scheduling table which is consulted by the technologist throughout the course of a day to schedule and keep track of required imaging tasks.

In addition to the scheduling table, often a hardcopy (i.e. paper) requisition form will be provided for the technologist which includes additional patient identifying information (e.g. weight, height, sex, etc.), may list allergies, identifies the type of exam (e.g. c-spine, brain, head) to be performed, identifies the requesting physician and so on. Prior to imaging a requisition form is required to ensure that inadvertent imaging is not performed on patients. Once again, some automated facilities provide a computer for accessing requisition forms.

After examining a requisition form and confirming authorization and prior to meeting a patient, the technologist typically confirms images which have to be acquired during a subsequent session. For example, while imaging a spinal section using the MR modality, it may be conventional to obtain a series of image slices along the length of the spinal section using a T1 FSE pulse sequence and a T2 FSE pulse sequence. In addition, a particular physician may routinely require a third series of image slices using an oblique axial FSE pulse sequence. To confirm required images technologists often consult a required image guidebook which includes lists of required images and may include lists of images specially required by specific radiologists. In addition, a guidebook may also indicate required patient position and equipment position for each required image. Moreover, each facility may also have a list of standard required images which must be consulted by the technologist.

During patient preparation and handling, the technologist greets the patient, explains the imaging procedure, helps the patient onto an imaging table and guides the patient into a first position required to collect a first of the required images.

Next, during acquisition the technologist typically uses an acquisition computer to select specific images to be generated by selecting image boundaries and image parameters. To this end the technologist often will acquire one or more localizing images which can be used to generally identify the position of anatomical structures within a patient's body. Viewing the localized image the physician selects required images to be generated and can select imaging parameters to use when generating the required images.

Typically there are many different imaging parameters which can be selected and adjusted. In an effort to make acquisition computers easy to use, many acquisition computers provide an interactive interface including parameter icons for use with a pointing device to enable a technologist to select icons and change parameters with the click of a pointing device button (e.g. a mouse) or via a keyboard. To notify a technologist of all selectable parameters and iconic parameter selecting tools, interfaces of this type display virtually all parameters and associated icons on the interface for examination selection.

In addition, to help a technologist select appropriate parameter settings, the imaging guidebook may also include tables indicating standard parameter settings for each image to be formed. These standards may be selected by the facility generally and may also include specific required settings for each requesting radiologist. After selecting parameters, the technologist causes the imaging system to acquire the selected images, the system storing the images electronically.

Next, the technologist may reposition the patient in a position optimal for collecting data for the second required image and thereafter follows the same procedure described above to collect required image data.

After required images have been stored electronically the images are downloaded onto an archive system which typically includes a second computer in addition to the acquisition computer. By downloading digital images to a second computer the acquisition computer is freed to perform a subsequent image acquisition. Many acquisition computers enable both archiving and acquisition at the same time so that, while image data corresponding to one patient is downloaded to the second computer, image data corresponding to another patient can be collected. This simultaneous dual function ability increases the throughput rate (i.e. patients/day) for the imaging system and thus overall efficiency.

After the images are downloaded to the second computer, the technologist can use the second computer to analyze the images and perform advanced image processing. Thus, for example, where ten parallel and adjacent MR images have been collected which define a three dimensional data array, a technologist may want to generate a maximum intensity projection (MIP) using three of the ten images. To this end the technologist selects the three images to form the MIP and instructs the second computer to combine the three images to form the MIP. Other advanced processes are possible and are contemplated.

After advanced processing, the technologist may select all or a subset of the original or advanced process images for generating film hardcopies for physician review. After selecting images for filming a filming machine, which is also controlled and maintained by the technologist, is used to generate required film pictures. After filming, the pictures are provided to a physician for examination and thereafter are archived in a patient's file. In addition to filming, some systems also enable digital archiving so that digital images can be reaccessed using a computer or the like for review or for subsequent advanced processing.

After a completed imaging session the technologist typically uses a binded logbook notebook to document the completed session by indicating the date, time, patient name and number, examination type and so on. Thus, for a specific modality a technologist has to interact with several specific tools including a schedule, requisition forms, an image guidebook, an acquisition computer, a second advanced processing computer, a filming machine, an archiving database and a logbook.

While learning to use these tools for a single modality is not terribly difficult, differences between similar tools used for different modalities complicates the process of becoming proficient in two or more modalities. Thus, for example, scheduling clipboards for one imaging system may be set up entirely differently than scheduling clipboards for another imaging system. Even where two imaging systems are both automated to include scheduling computers and even where each of the two automated systems are provided by the same vendor, each computer usually includes a different interface such that entry of scheduling information into the two computers is in a unique sequence and different information may be required for each system.

Similarly, each system may have an entirely unique type of requisition form such that locating form information is a tedious task. This is true of both paper forms and automated computerized systems.

Moreover, imaging guidebooks may be relatively complex and can become difficult to use as radiologist's particular requirements are added to the books. For example, at a large medical facility there may be more than 10 radiologists who routinely require MR imaging. While each of the radiologists typically will require some identical images when a specific exam type structure (e.g. c-spine) is performed, many of the radiologists may require additional specific images which the particular radiologist finds helpful during diagnosis. In addition, while, for each required image there might be a typical patient position which is usually used to acquire the image, each radiologist may also have a slightly different preferred position which, in the radiologist's judgment, yields a slightly better fmal image. In addition, where radiologist's require specific system parameter settings the technologist also has to consult imaging guidebook tables to determine required settings. Thus, a complete imaging guidebook would have to indicate, for each radiologist, required images for each body structure, where applicable, specific required patient positions for each required image and required parameter settings for each image.

Clearly, using imaging guidebooks is tedious work. Unfortunately, the difficulty of using such guidebooks is exacerbated by the fact that many of the guidebooks have unique forms, some systems include two or more guidebooks and many guidebooks can be supplemented as radiologists are added to or removed from the facility staff.

Moreover, acquisition computer interfaces are often very different and therefore, knowing how to use one interface does not render another interface intuitive. For example, the acquisition computers for a MR system and a CT system often have extremely different interfaces which require a technologist to step through very different protocols. This is not surprising as the parameters which have to be selected for different modalities often are different. However, the tools provided for setting even similar parameters on two different imaging systems often have a very different appearance and different operation. Thus, for example, to increase a displayed parameter value one interface may require a user to place a cursor in a parameter box and type in a desired value. Another interface may include up and down arrow icons adjacent a parameter box with a current parameter setting displayed in the box, the setting increased by selecting the up arrow via a pointing device.

Acquisition computer differences are exacerbated by the fact that most system interfaces are extremely cluttered as virtually every possible tool for setting acquisition parameters is usually provided on the interface screen, this despite the fact that many tools are only rarely used by the technologist. While designed to help a technologist by indicating all possible tools it has been recognized that such a crowded screen actually reduces technologist efficiency as the locations of the most widely used tools are obfuscated.

Furthermore, the interfaces and operation of the advanced processing computers, filming machines and archiving computers for different processes (i.e. modalities) are also often very different.

All of the interfacing problems described above are exacerbated where a single technologist works between facilities as facility unique interfaces, guidebooks and schedules have to be decrypted by visiting technologists prior to efficient system use.

Solutions to the problems described above have not heretofore included significant remote capabilities. In particular, communication networks, such as, the Internet or private networks, have not been used to provide remote services to such medical diagnostic systems. The advantages of remote services, such as, remote monitoring, remote system control, immediate file access from remote locations, remote file storage and archiving, remote resource pooling, remote recording, remote diagnostics, and remote high speed computations have not heretofore been employed to solve the problems discussed above.

Thus, there is a need for a medical diagnostic system which provides for the advantages of remote services and addresses the problems discussed above. In particular, there is a need for providing remote services in imaging systems with multiple modality interfaces. Further, there is a need for operating in a remote service mode in imaging systems.

SUMMARY OF THE INVENTION

One embodiment of the invention relates to an imaging system coupled to a network, the network coupling imaging devices of at least first and second different imaging modalities, each modality including functions which are common to each of the first and second modalities. The system includes an imaging device, a network coupling the imaging device to a remote facility, an interface associated with the imaging device, and a pointing device for moving a pointer icon about the display and for selecting displayed icons. The network provides the imaging device with remote services from the remote facility. The interface includes a display and a programmed data processor for providing a uniform interface image on the display despite the specific modality. The uniform interface image includes a function navigation space including function icons corresponding to procedures which are common to both the first and second imaging modalities and a workspace adjacent the function navigation space for displaying, analyzing and manipulating images of a type consistent with the specific modality. When an icon is selected, the processor correlates the selected icon with a corresponding command and executes the command.

Another embodiment of the invention relates to a method for use with a specific one of at least first and second specific imaging modalities, each modality requiring a modality specific imaging assembly, a processor, a display and a pointing device for moving a pointer icon about the display and for selecting displayed icons. The method guides a technologist through the processes required to use the modality specific imaging system and includes the steps of: providing an interface image on the display, providing a pointer icon on the display, and, when the pointer icon is used to select one of the function icons, correlating the selected icon with a corresponding command and executes the command. The interface image includes a function navigation space including function icons corresponding to procedures which are common to both the first and second modalities and a workspace adjacent the function navigation space for displaying, analyzing and manipulating images of a type consistent with the specific modality. One of the function icons provides for selection of a remote services mode.

Another embodiment of the invention relates to an imaging system coupled to a network. The imaging system includes an imaging device, a communications module coupling the imaging device to a remote facility, an interface associated with the imaging device, and a pointing device for moving a pointer icon about the display and for selecting displayed icons. The interface includes a display and a programmed data processor for providing a uniform interface image on the display despite the specific modality. The uniform interface image includes a function navigation space including function icons corresponding to procedures which are common to both the first and second imaging modalities and a workspace adjacent the function navigation space for displaying, analyzing and manipulating images of a type consistent with the specific modality. When an icon is selected, the processor correlates the selected icon with a corresponding command and executes the command.

Other principle features and advantages of the present invention will become apparent to those skilled in the art upon review of the following drawings, the detailed description, and the appended claims.

BRIEF DESCRIPTION OF THE DRAWINGS

Preferred exemplary embodiments are described below with reference to the accompanying drawings, wherein like reference numerals denote like elements, and.

DETAILED DESCRIPTION OF THE PREFERRED EMBODIMENT

Hardware

Figure 1:
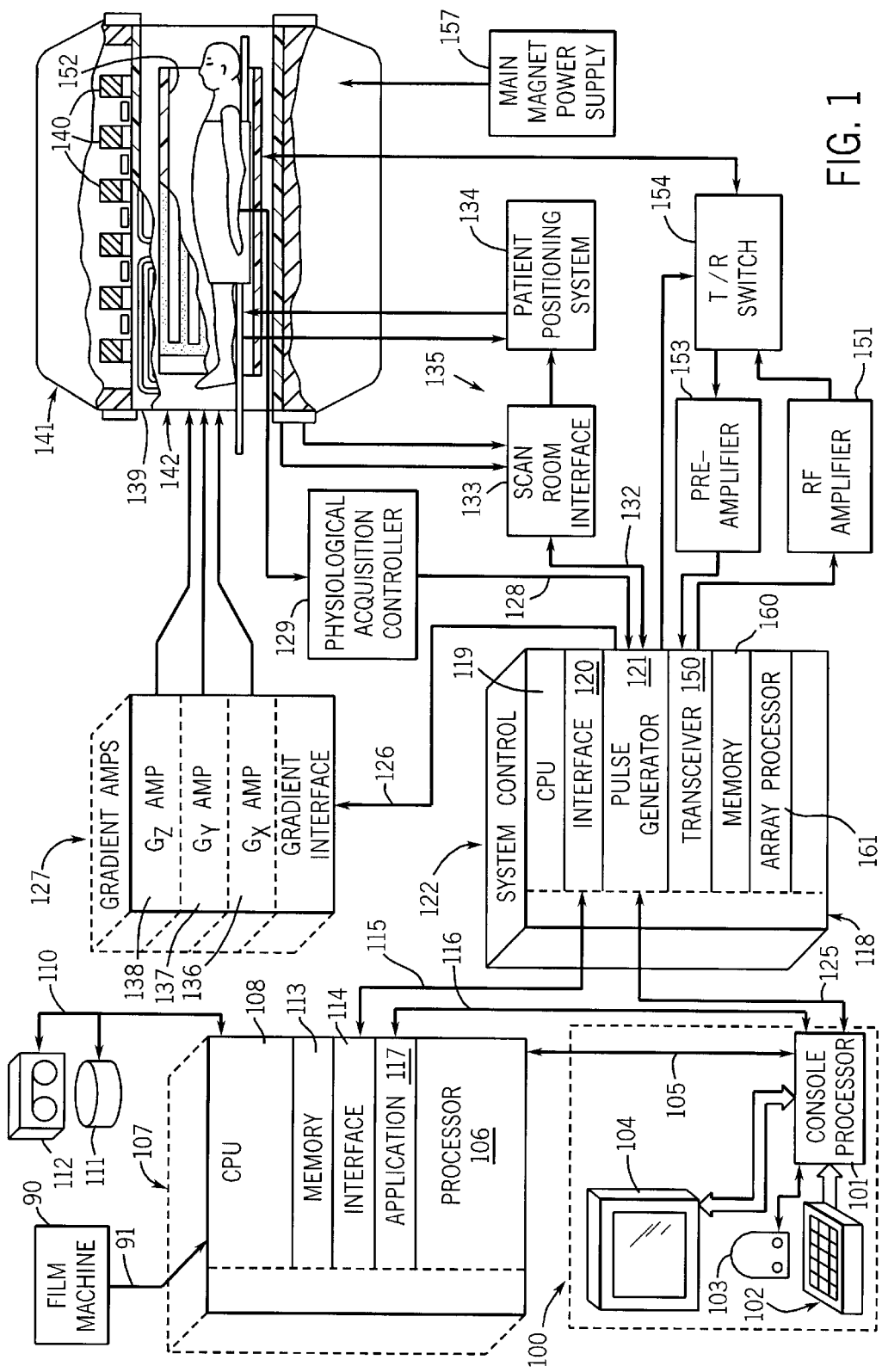
FIG. 1 is a block diagram of an MRI system which employs a preferred embodiment of the invention.

While the preferred embodiment of the present invention is meant to be used with any imaging system despite the modality facilitated by the system, in order to simplify this explanation the invention will be described in the context of an exemplary MR system. To this end, referring first to FIG. 1, there is shown the major components of a preferred MR system which incorporates the present invention. The operation of the system is controlled from a universal interface 100 which includes an interface processor 101 that scans a keyboard 102 and receives inputs from a human operator through a display screen 104. Screen 104 may be either a plasma/touch screen or a more conventional display on which a pointer cursor is provided which can be moved via mouse 103. For the purposes of the presently preferred embodiment it will be assumed that mouse 103 is used to move a pointing icon or cursor on display 104.

Interface processor 101 communicates through a communications link 116 with an applications interface module 117 in a separate computer system 107. Through the keyboard 102 and mouse 103, a technologist controls the production and display of images by a processor 106 in the computer system 107, which connects to display 104 through a video cable 105 and processor 101.

Computer system 107 includes a number of modules which communicate with each other through a backplane. In addition to application interface 117 and processor 106, these include a CPU module 108 which controls the backplane and which connects the computer system 107 through a bus 110 to a set of peripheral devices, including disk storage 111 and tape drive 112. CPU module 108 is also linked to a film machine 90 via a bus 92. The computer system 107 also includes a memory module 113, known in the art as a frame buffer for storing image data arrays, and a serial interface module 114 that links the computer system 107 through a high speed serial link 115 to a system interface module 120 located in a separate system control cabinet 122.

The system control 122 includes a series of modules which are connected together by a common backplane 118. The backplane 118 is comprised of a number of bus structures, including a bus structure which is controlled by a CPU module 119. The serial interface module 120 connects this backplane 118 to the high speed serial link 115, and pulse generator module 121 connects the backplane 118 to interface 100 through a serial link 125. It is through this link 125 that the system control 122 receives commands from the technologist which indicate the scan sequence that is to be performed.

The pulse generator module 121 operates the system components to carry out the desired scan sequence. Module 121 produces data which indicates the timing, strength and shape of the RF pulses which are to be produced, and the timing of and length of the data acquisition window. Module 121 also connects through serial link 126 to a set of gradient amplifiers 127 and conveys data thereto which indicates the timing and shape of the gradient pulses that are to be produced during the scan. The pulse generator module 121 also receives patient data through a serial link 128 from a physiological acquisition controller 129. The physiological acquisition control 129 can receive a signal from a number of different sensors connected to the patient. For example, it may receive ECG signals from electrodes or respiratory signals from a bellows and produces pulses for the pulse generator module 121 that synchronizes the scan with the patient's cardiac cycle or respiratory cycle. And finally, the pulse generator module 121 connects through a serial link 132 to scan room interface circuit 133 which receives signals at inputs 135 from various sensors associated with the position and condition of the patient and the magnet system. It is also through the scan room interface circuit 133 that a patient positioning system 134 receives commands which move the patient cradle and transport the patient to the desired position for the scan.

The gradient waveforms produced by the pulse generator module 121 are applied to a gradient amplifier system 127 comprised of $G_x$, $G_y$ and $G_z$, amplifiers 136, 137 and 138, respectively. Each amplifier 136, 137 and 138 is utilized to excite a corresponding gradient coil in an assembly generally designated 139. The gradient coil assembly 139 forms part of a magnet assembly 141 which includes a polarizing magnet 140 that produces either a 0.5 or a 1.5 Tesla polarizing field that extends horizontally through a bore 142. Operation of coils 139 is well known in the art and therefore is not explained here in detail.

Located within the bore 142 is a circular cylindrical whole-body RF coil 152. This coil 152 produces a circularly polarized RF field in response to RF pulses provided by a transceiver module 150 in the system control cabinet 122.

These pulses are amplified by an RF amplifier 151 and coupled to the RF coil 152 by a transmit/receive switch 154 which forms an integral part of the RF coil assembly. Waveforms and control signals are provided by the pulse generator module 121 and utilized by the transceiver module 150 for RF carrier modulation and mode control. The resulting NMR signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 which is also part of the system control 122. When the scan is completed and an entire array of data has been acquired in the memory modules 160, an array processor 161 operates to Fourier transform the data into an array of image data. This image data is conveyed through the serial link 115 to the computer system 107 where it is stored in memory 113. In response to commands received from interface 100, this image data may be archived on the tape drive 112 or memory 111, or it may be further processed by the image processor 106 and conveyed to interface 100 and presented on display 104.

Interface

A preferred embodiment of the present invention includes interface 100 and system 107 and is manifest in two general concepts, a universal interface and modality guidance tools which determine information which should be provided to a technologist via the universal interface during an imaging session.

With respect to the universal interface, processes which are common to virtually all imaging modalities have been identified, sub-processes which are common to each process in a specific modality have been identified and parameters which are common to each sub-process in a specific modality have been identified. Based on the common processes, sub-processes and parameters a set of interface screens have been developed which, despite use with each of the modalities, have many identical characteristics which are recognizable and foster a comfortable feeling, even for a technologist using a system for the first time.

With respect to the modality guidance tools, it has been recognized that each hospital, and perhaps each radiologist at a hospital, may require different images to be generated during a specific type of exam, may require specific patient positions during generation of data for certain images and may also require specific parameter settings for each image generated. The modality guidance tools consist of a set of tables stored in computer memory which are used to automatically determine required settings and images and for indicating suitable patient position-when a specific radiologist orders an exam of a specific type. After determining required images, positions and parameters using the guidance tools, icons are provided via the universal interface to guide the technologist through a properly orchestrated imaging protocol.

Figure 2:
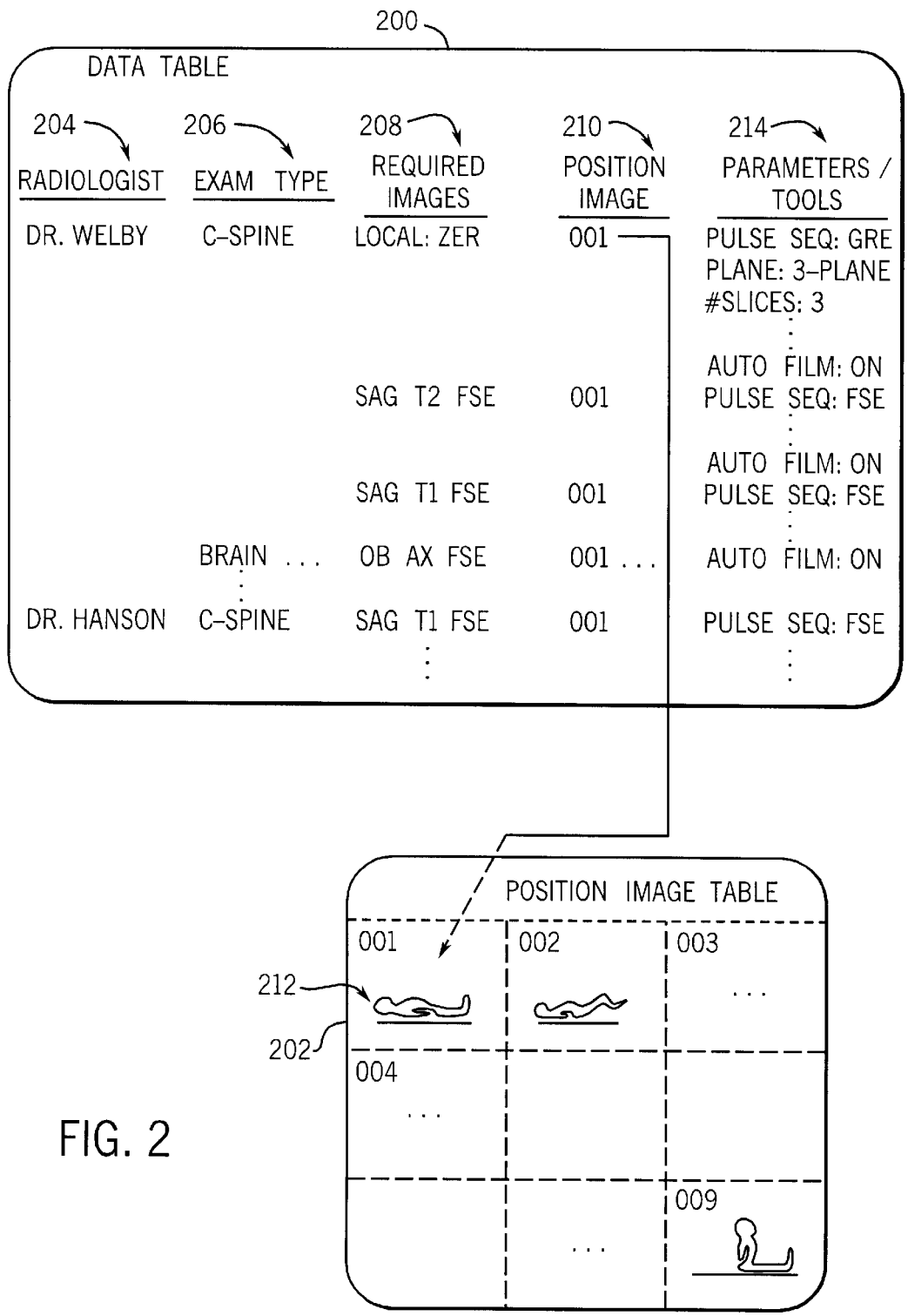
FIG. 2 is a schematic illustrating an exemplary data table and an exemplary position image table according to a preferred embodiment of invention.

Referring now to FIG. 2, therein are shown two exemplary tables stored in memory 113 which are accessible to processor 106 via the common backplane and which are used by processor 106 to provide interface information to console processor 101 for guiding a technologist through an imaging process. The two tables include a data table 200 and a position image table 202. Exemplary data table 200 includes five separate types of information. The first type of information includes radiologist indicators which, for the purposes of this explanation are shown as the names of different radiologists in a first table column 204. While two radiologist names, Dr. Welby and Dr. Hanson are shown, it is contemplated that there may be many more radiologists listed.

A second type of information includes exam types which are shown in a second column 206. For each doctor listed in first column 204, every possible type of exam is listed in second column 206. Exemplary exam types shown in FIG. 2 include a C-spine type and a brain type.

For each exam type listed in the second column 206, a plurality of required images are listed in a third column 208. For example, for Dr. Welby's C-spine exam type, required images include a saginal T2 FSE sequence, a saginal T1 FSE sequence and an oblique axial FSE sequence. Although not illustrated, a similar list of required images would be provided for Dr. Welby's brain type examination and for each of the other types of examinations Dr. Welby often requests. In addition, a similar list of required images would be provided for each exam type Dr. Hanson routinely requests and so on.

For each required image in third column 208 a position image address corresponding to an image stored in position image table 202 is provided. For example, for the saginal T2 FSE required image for Dr. Welby's C-spine exam type, the position image address in fourth column 210 is 001. Address 001 points to an image 212 in position image table 202 which is stored at address 001. Image 212 shows a patient laying flat on her back with legs extended on an imaging table. It should be noted that while image 212 and other images in position image table 202 are shown as simplified silhouette drawings, more detailed images are contemplated and in fact are preferred with the present invention. The more detailed images may include actual digital pictures of a model positioned in precisely required positions for imaging purposes. In addition, the position images may also include text descriptions of ideal patient positions to help a technologist identify an ideal position. Moreover, while a single position image table is illustrated in FIG. 2, memory 113 (see FIG. 1) may include a separate position image table for each radiologist listed in data table 200. Furthermore, the position images in table 202 may also indicate desired equipment positions relative to a patient (e.g. location of a CT camera relative a patient).

Referring still to FIG. 2, for each required image in third column 208, a plurality of tools and default parameter settings for a specific radiologist and specific exam type are listed in fifth column 214. Importantly the parameters listed in fifth column 214 are only the most important parameters and the most often modified parameters for a particular imaging modality. The tools listed in column 214 are the tools which are necessary for modifying the default parameter values.

It should be appreciated that while the tables shown in FIG. 2 provide data and position images for each radiologist for MR imaging, a separate yet similar table is provided for each of the other six imaging modalities in imaging system memories earmarked specifically for those other modalities. For example, a CT system would include tables similar to table 200 and 202 which identify each radiologist, exam types, required images, position image specifiers and parameters and tool specifiers.

Figure 3:
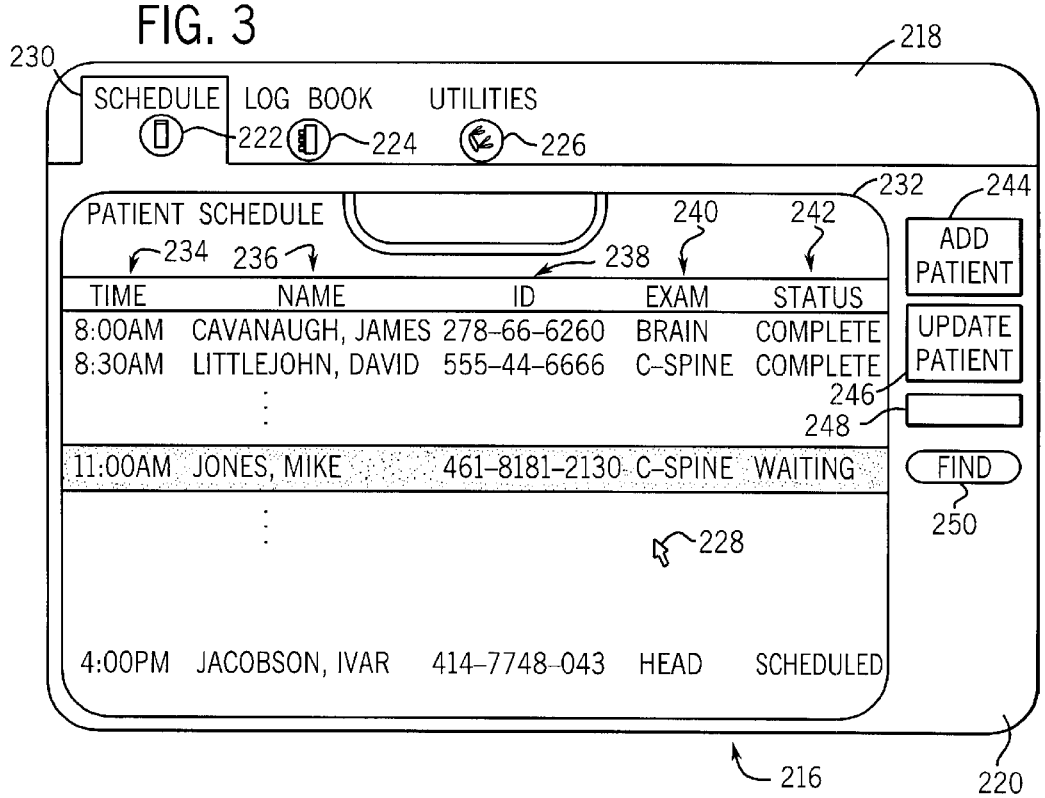
FIG. 3 is a schematic illustrating an exemplary schedule interface screen according to the preferred embodiment of invention.

Referring now to FIG. 3, an exemplary interface screen 216 which is provided on display 104 is illustrated. Screen 216 generally includes two spaces including a domain space 218 and a dynamic space 220. Generally, within domain space 218, three separate domain icons including a schedule icon 220, a log book icon 224 and a utility icon 226, are provided. Each of the domain icons 222, 224 and 226 can be selected by using mouse 103 (see FIG. 1) to move a pointing cursor or icon 228 about screen 216. Each of domain icons 222, 224 and 226 is used to open an entirely different application of the inventive interface system. Generally, schedule icon 222 enables a technologist to review and modify a patient schedule corresponding to a specific imaging system. Log book 224 enables a technologist or radiologist to review a log book of completed imaging sessions and, where images are digitally archived, enables the technologist to retrieve and review the archived images. Utilities icon 226 allow the technologist to perform a number of tasks including, but not limited to, retrieving archived records and modifying the default settings which are illustrated in the tables of FIG. 2.

Initially, when a technologist logs on to interface 100, the technologist is provided with a simple screen including domain space 218, dynamic space 220 and the domain icons 222, 224 and 226 spaced in a single row within domain space 218. Spaces 218 and 220 are differently colored to easily distinguish there boundaries.

Referring still to FIG. 3, when schedule icon 222 is selected processor 106 accesses a current patient schedule which is stored in memory 113 and performs four separate functions via control processor 101 which are observable on screen 216. First, processor 106 indicates selection of the schedule icon 222 by providing a "digital tab" 230 which encompasses the schedule icon 222 within dynamic space 220 to distinguish selected icon 222 from the non-selected icons 224 and 226 which remain within domain space 218. Second, processor 106 displays the current patient schedule on a digital clipboard metaphor image 232. Metaphor image 232 resembles a conventional hardcopy clipboard which is typically used by technologists to maintain a patient schedule. The schedule on image 232 may include any of several of different types of information, the exemplary schedule of FIG. 3 including a time column 234, a patient name column 236, a patient ID column 238, an exam type column 240 and a status column 242 which indicates whether or not an imaging session has been completed, is in a waiting state or is scheduled for a subsequent time.

Third, processor 106 provides display modifying icons including an add patient icon 244 and an update patient icon 246 which can be used to modify the schedule on image 232. Although not illustrated, it is contemplated that when one of the modify icons 244 or 246 is selected, a window opens up which provides tools to enable a technologist to add, delete or modify information corresponding to any of the information listed on image 232. Methods and software for performing these tasks are well known in the art and therefore are not explained here in detail.

Fourth, processor 106 provides a search box 248 and a find icon 250 which can be used together to locate a specific patient on patient schedule image 232. To this end, a patient's name can be provided in box 248 and thereafter icon 250 can be selected at which time processor 106 searches the table stored in memory 113 and locates the indicated patient.

In addition to the four identified processor functions which are recognizable via display 104, processor 106 also provides a memory 113 address for each patient exam provided on image 232, the memory address invisible to the technologist but nevertheless linked to a specific exam. A specific exam and associated memory address operate like an Internet hyperlink to allow a technologist to access a radiology request form associated with the specific exam and stored at the memory address by selecting the specific exam using icon 228.

Referring to FIGS. 1 and 3, using mouse 103 a technologist can select any of the icons illustrated on screen 216 by placing icon 228 on the illustrated icon and pressing a recognizable sequence of mouse buttons. While schedule image 232 is being examined, a technologist can place pointing cursor 228 on any patient name which appears on image 232 and, by selecting the patient's name, can access a digital radiology request form corresponding to the patient and the specific exam. In particular, prior to every imaging session, a technologist must review a radiology request form 0o make sure that the imaging session has been authorized by one of the radiologists and to identify any special instructions provided by the radiologist. In FIG. 3, it is assumed that for each exam having a "complete" status, the technologist has already reviewed a radiology request form, met with the patient, set up an exam, performed an imaging session to generate imaging data and has downloaded the imaging data to either of devices 111 or 112. However, for the exams having a "waiting" status Indicator in column 242 of image 232, the technologist has not yet accessed a radiology request form.

To access the radiology request form, as indicated above, the technologist uses cursor 228 to select the next exam having a "waiting" status in image 232. In this case, the technologist selected Mike Jones. When selected, the entire row of data in image 232 corresponding to Mike Jones is highlighted. A second selection causes processor 106 to move from a scheduling domain into an imaging session domain.

Figure 4:
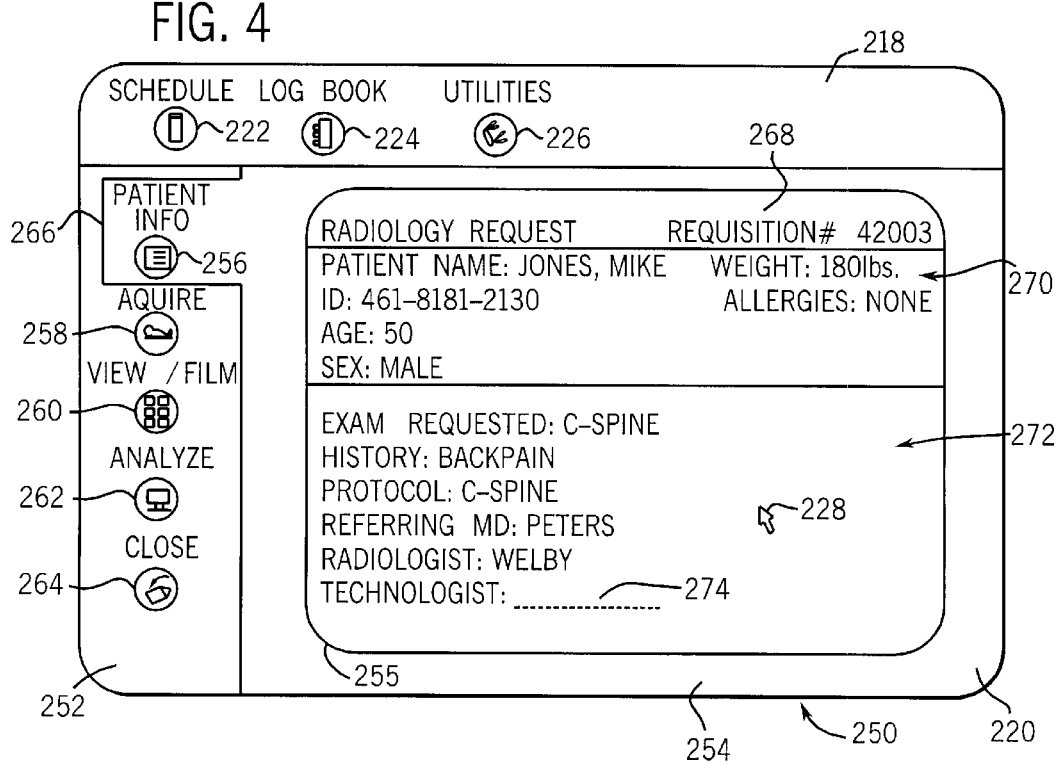
FIG. 4 is a schematic illustrating an exemplary patient information interface screen.

Referring now to FIG. 4, an interface screen 250 provided by processor 106 when Mike Jones is selected via image 232 is illustrated. Screen 250 includes both the domain space 218 and the dynamic space 220. However dynamic space 220 is now divided into a primary navigation space 252 which, in the exemplary illustration, includes a single column along the left-hand side of dynamic space 220 and a work space 254.

Processor 106 provides a plurality of function icons in navigation space 252. Importantly, the function icons in space 252 have been selected to mirror processor functions which are common to virtually all imaging modalities. Therefore, the navigation space icons can be provided on separate interfaces corresponding to every type of imaging system. Thus, for example, while the interface screen 250 shown in FIG. 4 is specifically for an MR system, an interface having both the domain space 218, including icons, and the navigation space 252, including navigation space icons, would be provided for a CT interface, a radiography interface, a fluoroscopy interface and so on. This feature which clearly defines specific and common functions between all imaging systems fosters a sense of comfort when a technologist moves from one imaging system type to another imaging system type or from one medical facility to another. This common interface also helps guide the technologist through an imaging session.

Referring to FIG. 4, the navigation space icons includes a patient information icon 256, an acquire icon 258, a view/ film icon 260, an analyze icon 262 and a close icon 264. It should also be noted that all of the navigation space icons are arranged in a single column which follows a normal workflow pattern from the patient information icon 256 through the acquire icon 258, the view/film icon 260, the analyze icon 262 and the close icon 264. This feature enables a technologist to clearly see a required or desired workflow pattern.

Referring to FIGS. 1, 3 and 4, when a technologist selects Mike Jones on interface 262 processor 106 accesses memory 113 and retrieves the radiology request form which is stored at the address corresponding to the exam for Mike Jones. Retrieving the radiology request form processor 106 displays the request form in workspace 254. In addition, to clearly indicate that the information in workspace 254 is associated with the patient information icon 256, processor 106 encompasses patient information icon 256 in workspace 254 by providing a digital tab 266 which includes patient information icon 265 in workspace 254.

Referring still to FIG. 4, an exemplary radiology request form 255 includes a requisition number 268, patient identification information (e.g. name, id number, age, weight, etc.) generally referenced by numeral 270 and exam request information indicating the type of exam required, relative patient history, a required protocol, the referring doctor, the responsible radiologist and so on, collectively referred to by numeral 272. In addition, processor 106 may include a space 274 where the technologist can input her name to complete the radiology request form. Although not illustrated, iconic tools for modifying the protocol or other request form information may be provided within workspace 254, the tools selectable via pointer icon 228.

Figure 5:
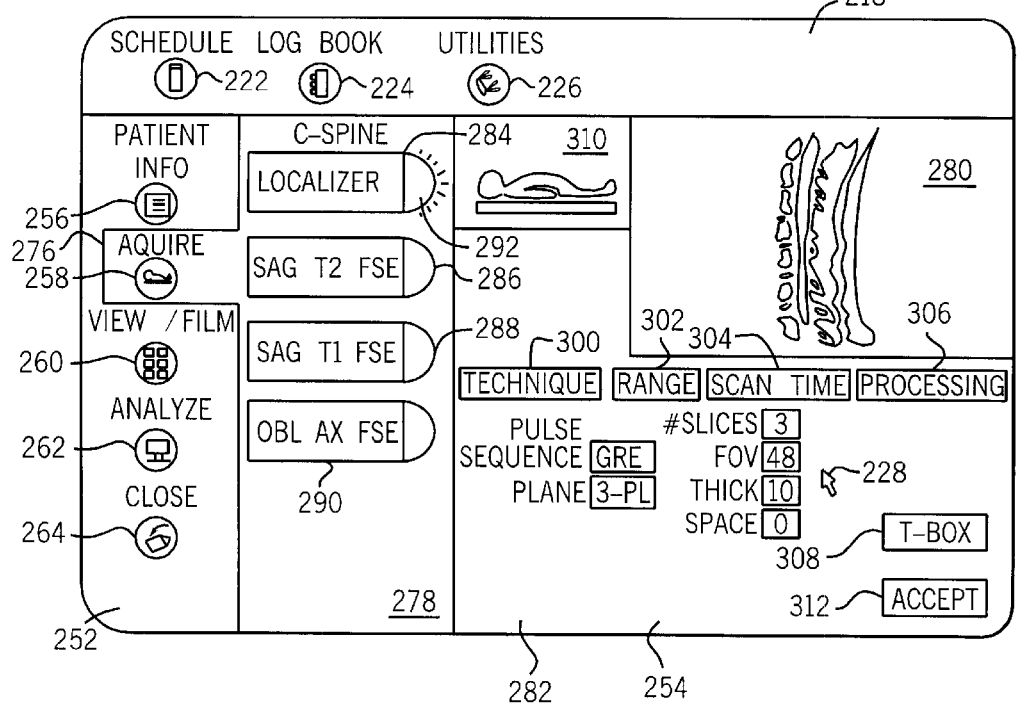
FIG. 5 is a schematic illustrating an exemplary acquire interface screen.

After the technologist has examined the radiology request form to determine a required protocol and ensure proper authorization of the exam, the technologist selects acquire icon 258 via icon 228. Referring now to FIG. 5, when acquire icon 258 is selected, processor 106 indicates selection of acquire icon 258 by providing a digital tab 276 which encompasses acquire icon 258 within workspace 254. In addition, processor 106 divides workspace 254 into a workflow navigation space 278, an imaging window 280 and a parameter settings space 282. Workflow navigation space 278 preferably includes a single column adjacent navigation space 252. In the exemplary illustration, the imaging window is in the upper right-hand corner of workspace 254 while parameter settings space 282 encompasses the remainder of workspace 254.

Referring now to FIGS. 1, 2, 4 and 5, in addition to dividing workspace 254 as described above, when acquire icon 258 is selected, processor 106 identifies the radiologist indicated on the request form 255 and the required protocol from the request form and uses those two pieces of information to access a specific set of required images and parameters in table 200 which is stored in memory 113. In the present example, processor 106 identifies Dr. Welby and his C-spine protocol as the exam type and accesses memory 113 to identify four required images including a "localizer" a "Sag T2 FSE", a "Sag T1 FSE" and a "ob ax FSE" image. For each of these required images, processor 106 provides a separate icon within space 278. The icons are identified by numeral 284, 286, 288 and 290, respectively and are collectively referred to as a workflow icon set. Each of the workflow icons includes a virtual button and an LED illustration which, when the icon is selected, lights up. For example, localizer icon 284 includes LED illustration 292.

Importantly, just as the function icons in navigation space 252 are provided in a typical workflow form from top to bottom, workflow icons in space 278 are also provided in a similar top to bottom workflow pattern. To this end, localizer icon 284 is first listed and therefore generally first selected to generate a "localizer" image in image window 280 which ca be used to determine general patient and anatomical body position with respect to system hardware. Thereafter other icons 286, 288 and 290 are selected to generate three different types of image sets and the typical order is Sag T1 FSE, Sag T2 FSE and ob ax FSE.

Referring to FIGS. 1, 2 and 5, initially, when localizer icon 284 is selected, no image is provided in window 280. However, all of the parameters and tools indicated in the fifth column 214 of table 200 which correspond to the localizer image for Dr. Welby's C-spine type exam are provided in space 282. All of the parameter values provided are the default values indicated in table 200. Each of the parameter values can be changed using iconic tools provided in space 282. For example, to change the pulse sequence of the plane through which a localizer image is taken, a technologist can select a technique tool icon 300 via icon 228. Although not illustrated, when one of the tool icons such as technique icon 300 is selected, it is contemplated that a window opens up providing tools to modify all of the parameters corresponding to technique (e.g. pulse sequence and plane). Similarly, a range tool icon 302 is provided, a scan tool icon 304 and a processor tool icon 306 each of which, when selected, opens a window for modifying parameters associated therewith.

Referring still to FIGS. 2 and 5, the parameter values and tools in space 282 are referred to generally as a commonly modified parameter set and associated tools. In addition to displaying all of the parameters values and tools indicated in column 214 of table 200 in space 282, processor 106 also provides a tool box icon 308 which, when selected, opens another window which includes a relatively large number of additional parameter values and tools which are only seldomly used during localizer imaging. These additional values and tools are referred to generally as a seldomly modified parameter set and associated tools. The idea here is that by providing seldomly used tools in a hidden yet easily accessible format (i.e. "behind" a tool box icon), the screen display is less cluttered and routinely used tools and selected parameters can easily be located. Preferably processor 106 also provides an image position window 310 in space 282 which indicates a patient position via an image from the position image table 202 which is indicated in fourth column 210 of data table 200. In the present example the displayed image in window 310 is the first image in position image table 202 as indicated in column 210.

Thus, after selecting localizer icon 284 the technologist can observe the image in window 310 to determine the correct position for the patient and can review all of the default settings for the exam type for the particular radiologist. If the radiologist requested specific parameter values which are different than the default settings, the technologist can use the iconic tools to modify the parameter values. Once the patient is properly positioned and all of the parameter values are properly set, the technologist selects an accept icon 312 indicating to the imaging system that a localizer image should be generated.

Thereafter, a localizer image is generated via the system of FIG. 1 and the image appears in window 280 which is observed by the technologist. If desired, the technologist can generate several different localizer images until patient and anatomical body position is well known.

Next, referring to FIGS. 2 and 5, after a suitable localizer image has been generated, the technologist selects icon 286 to set up the Sag T2 FSE imaging session and then generates the required image set. Although not illustrated, when icon 286 is selected, processor 106 provides space 282 in a manner similar to that illustrated in FIG. 5, albeit providing parameter values, tools and a position image window corresponding to the data stored in table 200 which is associated with the Sag T2 FSE required image set. Again, with the parameter values, tools and position image provided in space 282, the technologist positions the patient accordingly and may modify some of the default parameters prior to selecting the accept icon 312 to generate a series of images corresponding to the desired protocol.

A similar process is performed to generate a series of images for each of the Sag T1 FSE and Ob Ax FSE icons 288, 290, respectively. All of the generated images are stored in memory 113.

Figure 6:
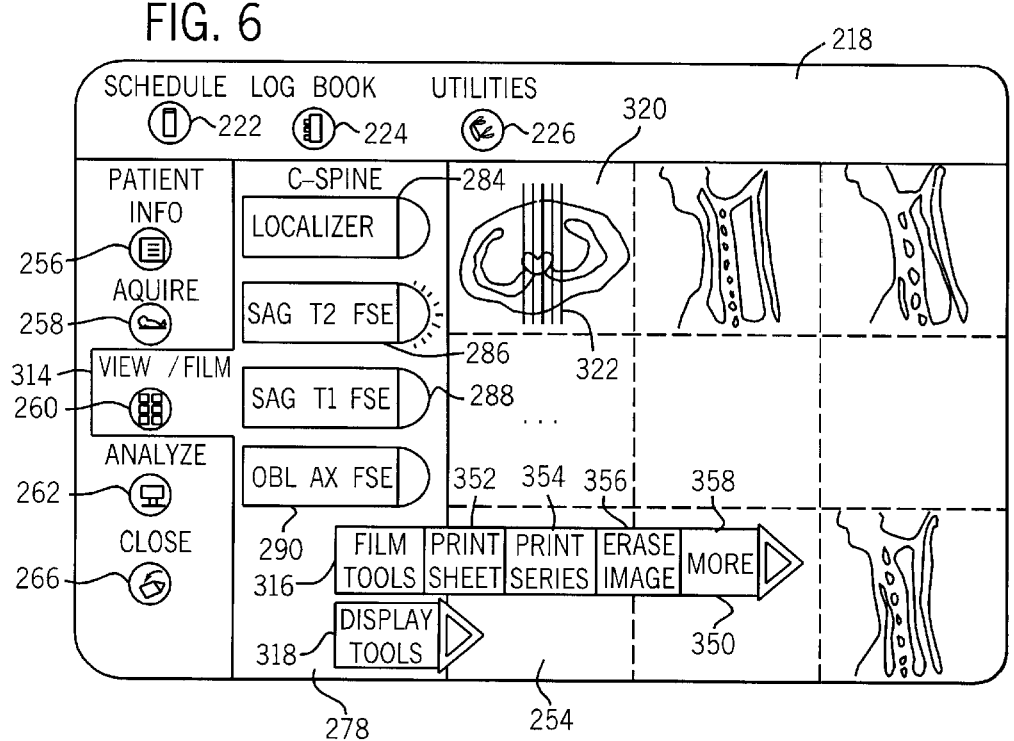
FIG. 6 is a schematic illustrating an exemplary image viewing display screen.

Referring now to FIG. 6, after all of the data or all of the required images has been collected and stored in memory 113, the technologist selects the view/film icon 260 to review the collected images. When icon 260 is selected, processor 106 indicates selection of icon 260 by providing a digital tab 314 which encompasses icon 260 in workspace 254. In addition, processor 106 maintains workflow icons 284, 286, 288 and 290 in space 278. Processor 106 also provides film and display tool icons 316 and 318, respectively, behind which various tools are hidden in window form, the tools described in more detail below.

The technologist can select any of the workflow icons 284, 286, 288 or 290 to display corresponding images in space 254. As illustrated, when icon 286 is selected, an image in a first box 320 includes an axial slice through a patient and provides phantom lines collectively referred to by numeral 322, each of the lines 322 corresponding to a separate one of the following images displayed in space 254. Processor 106 divides space 254 equally into a plurality of separate spaces and provides a separate image in each one of the spaces, each image corresponding to a separate one of lines 322.

After reviewing images, a technologist can use interface 100 to perform advanced processing techniques on the images thereby generating even more informative images for a radiologist to use. To this end, referring to FIG. 7, a technologist selects analyze icon 262. Referring also to FIG. 1, when icon 262 is selected, processor 106 indicates selection of icon 262 by providing a digital tab 324 which extends from workspace 254 and encompasses icon 262. In the interest of simplifing this explanation, while each separate radiologist at a facility may have a specific set of advanced imaging processes that the radiologist routinely like to have performed, it will be assumed that in this case the protocol for advanced image processing for each exam type is specified by the facility and is not radiologist dependent. Thus, for a C-spine exam type, the advanced imaging protocol is identical for every radiologist at the facility. While this assumption is made in the interest of simplifying this explanation it should be recognized that a table similar to the table illustrated in FIG. 2 could be provided in memory 113 (see FIG. 1) which would be accessed by processor 106 each time the analyze icon 262 is selected. In this case, the processor 106 would identify radiologist and exam type and access an advanced imaging table to determine a required and radiologist/exam type specific advanced imaging protocol. Thereafter, the processor 106 would provide a workflow icon for each step in the advanced imaging protocol in a workflow navigation space.

In the present example it will be assumed that for a C-spine examination at Dr. Welby's medical facility the standard protocol for all radiologists includes five steps which include, in the order of normal workflow, building a three-dimensional data model, isolating a right artery, rotating and filming the right artery, isolating a left artery and rotating and filming the left artery. To this end, processor 106 provides five workflow icons in workflow navigation space 278, the icons including a build model icon 326, an isolate right icon 328, a cine/film right icon 330, an isolate left icon 332 and a cine/film left icon 334.

Figure 7:
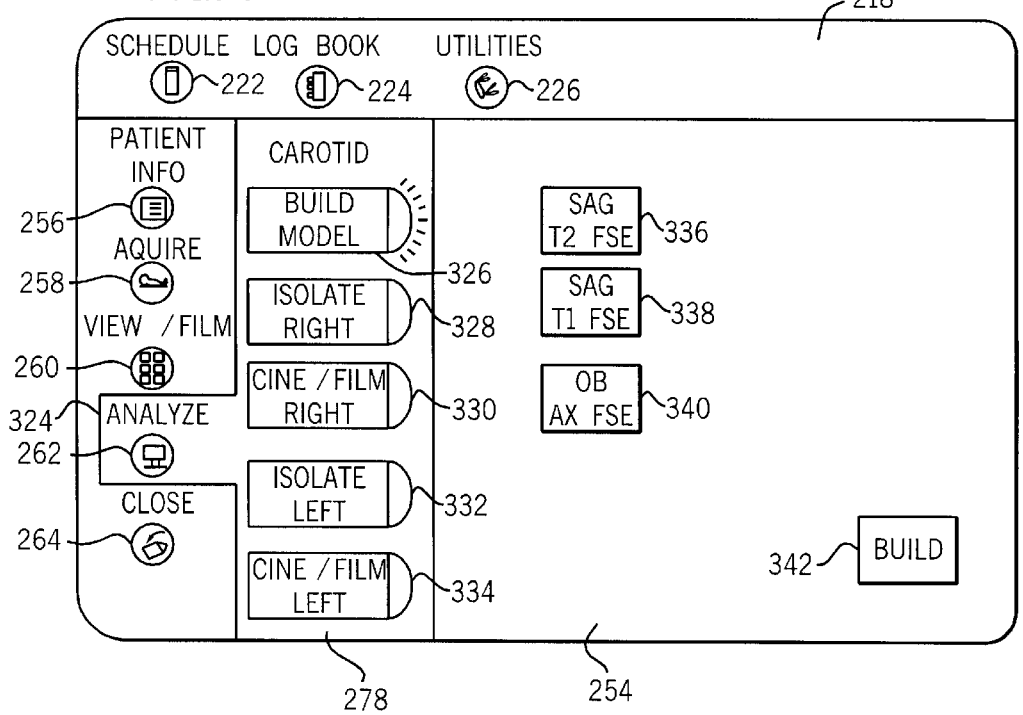
FIG. 7 is a schematic illustrating an exemplary analyze interface screen.

Referring still to FIG. 7, when the build model icon 326 is selected, processor 106 provides three tool icons 336, 338 and 340 in work space 254. Referring also to FIG. 6, icon 336 corresponds to all of the images in the image set associated with the Sag T2 FSE protocol. Similarly, icons 338 and 340 correspond to all of the images associated with the Sag T1 FSE protocol and the Ob Ax FSE protocol, respectively. The technologist selects one of icons 336, 338 or 340 to identify images which will be used to build the three-dimensional model and thereafter selects a build icon 342 instructing 106 to use the selected image set to build a three-dimensional model.

After the three-dimensional model is generated and stored in memory 113 the technologist steps through each of the isolate right icon 328, cine/film right icon 330, isolate left icon 332 and cine/film left icon 334 to select the specific portions of the three-dimensional model for imaging and to generate images of the selected portions. Isolating, rotating and filming are processes which are well known in the art and tools therefore are also well known in the art and therefore those processes and tools are not explained here in detail. It should be sufficient to state that all of the tools and an image display window for performing each of those processes would preferably be provided within space 254.

Referring once again to FIG. 6, after performing advanced image processing on the images the technologist selects the view/film icon 260 once again to display the original images or the advanced processed images within space 254. Where advanced processed images have been generated, another workflow icon (not illustrated) would be provided below icon 290 which could be selected by the technologist to view the advanced process images.

Having selected the view/film icon 260, processor 106 again enables the technologist to select any of the workflow icons 284, 286, 288 or 290 to view corresponding images. In FIG. 6 icon 286 has been selected and therefore corresponding images are illustrated. With the images illustrated, the technologist can select display tools icon 318 which opens a window (not illustrated) including a plurality of other tools that allow a technologist to examine displayed images. For example, one of the tools may be a measuring tool which allows a technologist to select two points on an image and measure the distance therebetween. Tools of this nature are well known in the art and therefore are not described here in detail.

In addition, with images displayed, the technologist may select the film tools icon 316 which opens a film tools window 350 as illustrated. Window 350 includes filming tools including a print sheet icon 352, a print series icon 354 an erase image icon 356 and a more icon 358. When print sheet icon 352 is selected, processor 106 provides data corresponding to every image in space 252 to film machine 90 and causes film machine 90 to generate either one or a plurality of hardcopy film images of the displayed imaged. When print series icon 354 is selected, processor 106 downloads data corresponding to all images corresponding to all of the workflow icons in space 278 to film machine 90 thereby causing machine 90 to generate hardcopy film images of each corresponding image. To use icon 356, first a technologist would select one or a plurality of images displayed within space 254 and thereafter select icon 356 to erase the selected image from space 254. It so contemplated that other filming tools could be accessed by selecting the more icon 358.

Referring again to FIG. 3, after filming is complete the imaging process is essentially completed for the patient and the process would begin again with the next patient on schedule image 232.

Referring again to FIGS. 1 and 3, when a technologist selects logbook icon 224, although not illustrated, processor 106 indicates selection of icon 224 by providing a digital tab which extends from space 220 and encompasses icon 224. In addition, processor 106 generates a logbook metaphor image (not illustrated) which is similar to the patient's schedule metaphor image 232, the logbook metaphor image provided in dynamic space 220. To distinguish the logbook metaphor image from the schedule image 232, preferably the logbook image has a slightly different appearance. For example, the logbook metaphor image may include a spiral binder appearance along the lefthand edge of the image. Information provided on the logbook image is similar to the information provided on patient schedule image 232 except that the logbook information includes information corresponding to completed imaging sessions. To this end, exemplary logbook image information may include a date, a patient's name, the patient's ID number, an exam type (e.g. brain, head, C-spine, etc.) and a column for indicating whether or not exam images have been archived.

Figure 8:
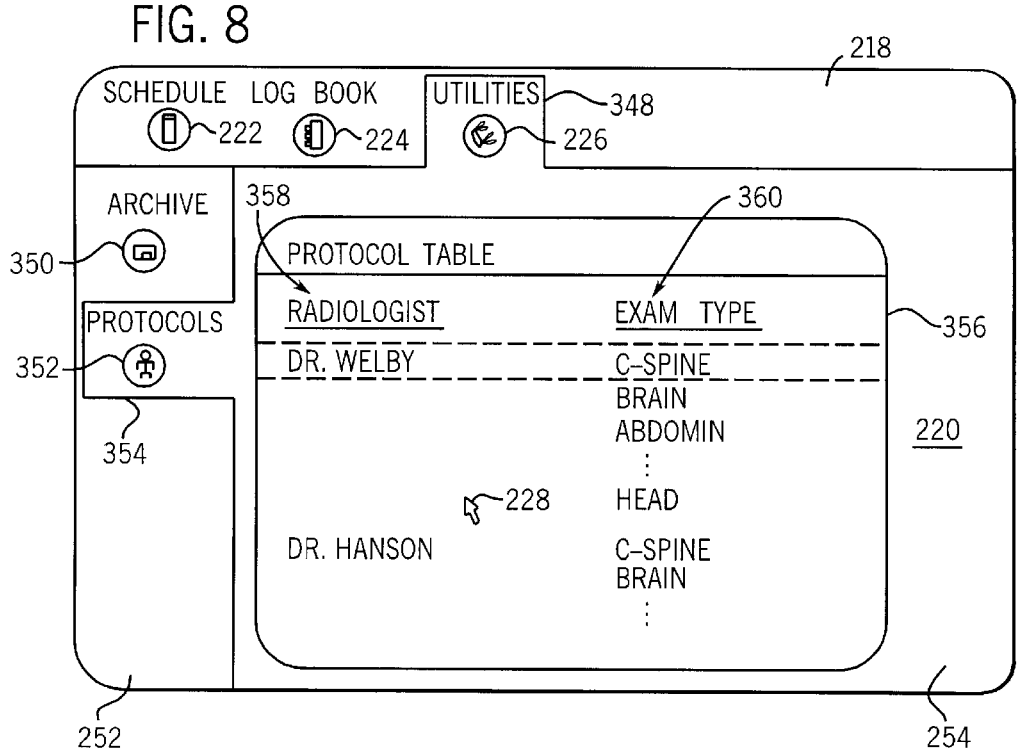
FIG. 8 is a schematic illustrating an exemplary utilities/protocol interface screen.

Referring now to FIG. 8, when a technologist selects utilities icon 226, processor 106 indicates selection by providing a digital tab 348 which extends from space 254 into domain space 218 and encompasses utilities icon 226. Utilities applications associated with icon 226 may include a number of different functions, two exemplary functions including an archive function and a protocols function which are used to store or retrieve images and to modify data and image tables (see FIG. 2), respectively. To this end, when utilities icon 226 is selected, processor 106 again separates dynamic space 220 into a navigation space 252 and a work space 254. Processor 106 provides both an archive icon 350 and a protocols icon 352 in space 252. Each of icons 350 and 352 selectable using icon 228. When archive icon 350 is selected, processor 106 provides iconic tools within workspace 254 which enable a technologist to retrieve and view archived images corresponding to previously performed imaging sessions. Tools for this purpose are known generally in the art and therefore are not described here in detail.

It is contemplated that a medical facility would likely have a set of internal policies concerning which personnel are authorized to modify default exam protocols and parameter values in data tables like table 200 illustrated in FIG. 2 for semi-permanent storage in memory 113. For example, one broad rule might be that only a radiologist is authorized to modify her default protocols and parameter values. To enforce such a rule a password security feature may be provided when protocols icon 352 is selected, processor 106 only allowing protocol modification by an authorized radiologist. While a secure system is preferred, it will be assumed that a technologist can modify default protocols and parameter values in table 200 to simplify this explanation.

When a technologist selects icon 352, processor 106 provides a digital tab 354 which extends from workspace 254 into space 252 and encompasses icon 352. In addition, processor 106 provides a protocol table 356 which corresponds to data table 200 in FIG. 2. The exemplary protocol table 356 includes two columns, first column 358 listing facility radiologists identified in table 200 and a second column 360 listing exam types (e.g. C-spine, brain, etc.) routinely requested by a corresponding radiologist. To modify the default settings within table 200, the technologist uses icon 228 to select a particular radiologist and exam type. For example, a technologist may wish to modify the default settings for Dr. Welby's C-spine exam type. To this end, the technologist selects Dr. Welby's C-spine from table 356.

Figure 9:
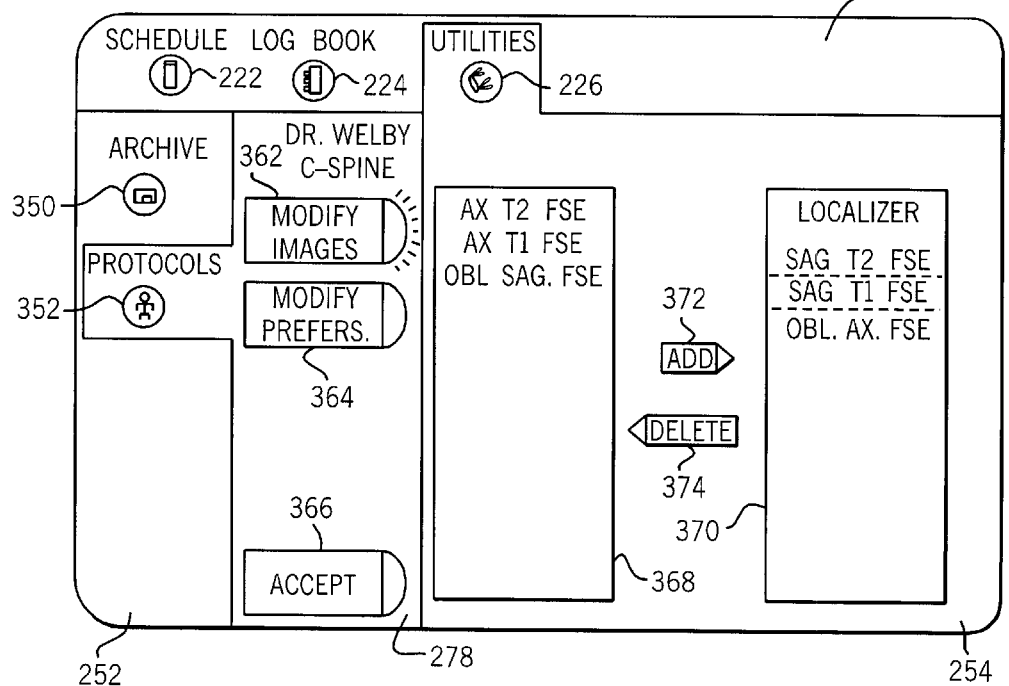
FIG. 9 is similar to FIG. 8, albeit illustrating a second level of the protocol interface screen.
Figure 10:
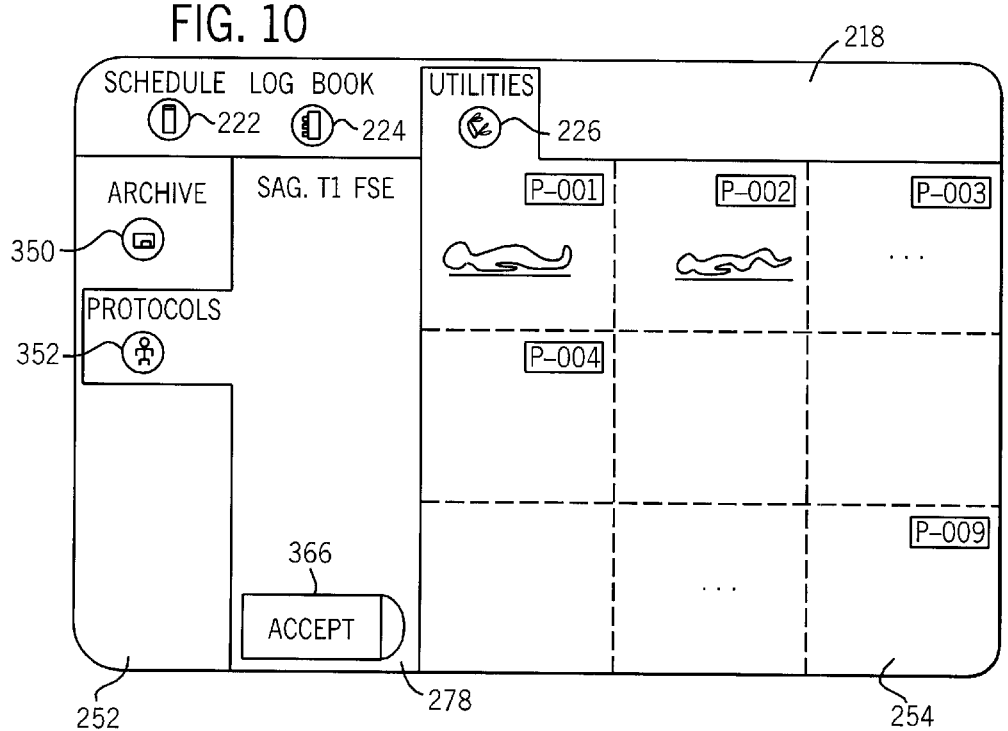
FIG. 10 is similar to FIG. 9 albeit illustrating yet another level of the protocol interface screen.

Referring now to FIG. 9, when Dr. Welby's C-spine exam is selected, processor 106 provides a modify images icon 362, a modify preferences con 364 and an accept icon 366 in workflow navigation space 278. In addition, processor 106 provides two tables, a first table 368 indicating additional image types which may be required and a second table 370 indicating already selected required image types for Dr. Welby's C-spine exam. Add and delete icons 372 and 374 are also provided. By selecting an image type in table 368 and then selecting the add icon 372, the tools for modifying the parameter values. Once the parameter values have been set, the technologist again accepts the values by selecting an icon similar to accept icon 366 which returns the technologist back to the screen illustrated in FIG. 9.

Referring still to FIGS. 2 and 9, to accept all of the changes made to table 200, the technologist selects accept icon 366 once again at which point processor 106 provides the screen illustrated in FIG. 8. Other modifications to protocols can be made in a similar fashion.

It should be appreciated that the above-described interface can be used to simplify technologist training thereby enabling less expensive technologist cross-training between imaging system modalities and enabling interfacility technologist substitution with relatively little difficulty. The guidance tools which consist primarily of guidance tables similar to those illustrated in FIG. 2 and an easily understood workflow which is presented in function and workflow icons through the inventive universal interface enable easy cross-training and interfacility substitutions.

Figure 11:
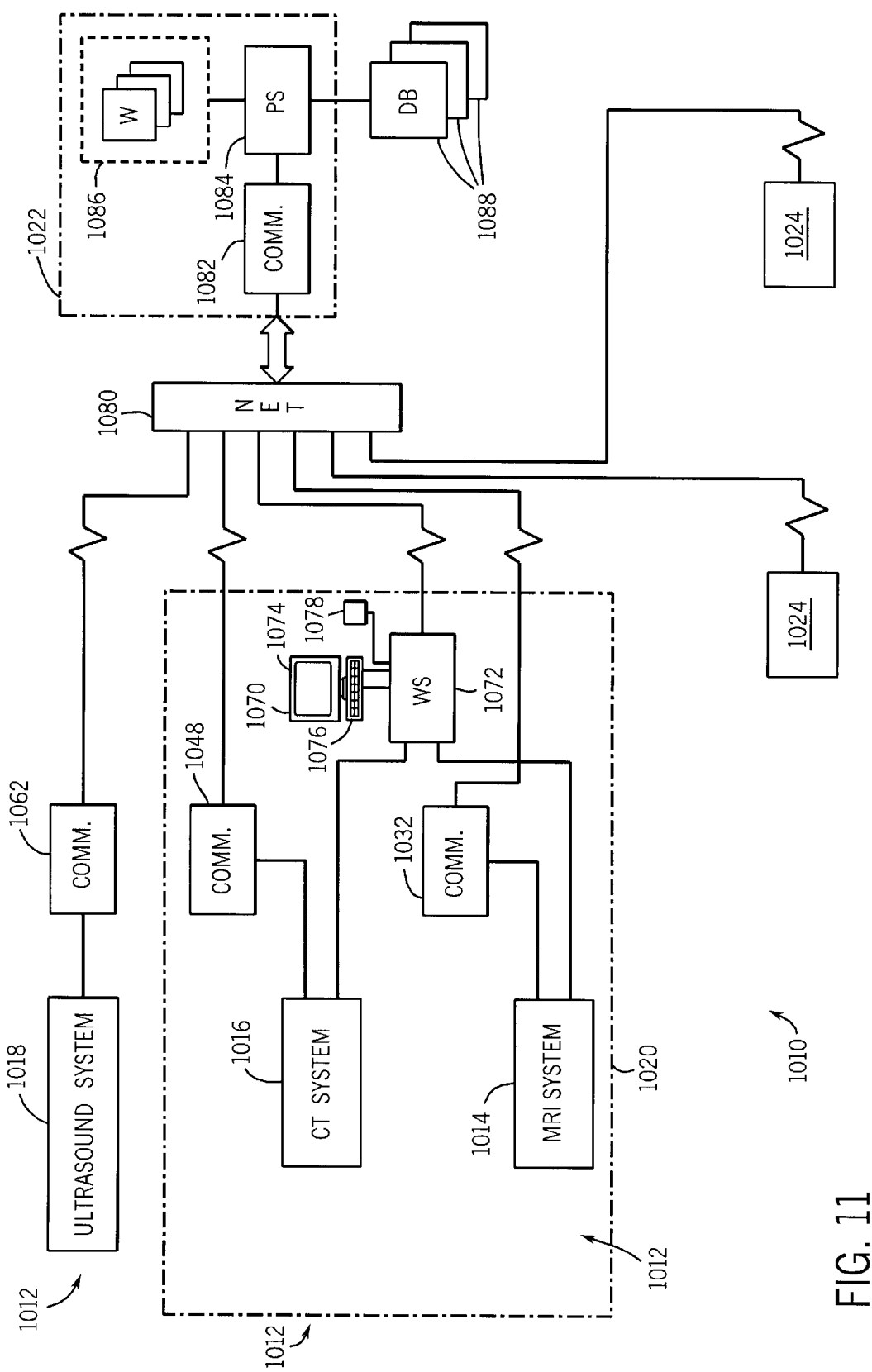
FIG. 11 is a diagrammatical representation of a series of medical diagnostic systems coupled to a service facility via a network connection for providing remote services and data interchange between the diagnostic systems and the service facility.

Referring now to FIG. 11, a service system 1010 is illustrated for providing remote service to a plurality of medical diagnostic systems 1012, including systems such as the MR system described with reference to FIG. 1, including interface 100 and system 107. In the embodiment illustrated in FIG. 11, the medical diagnostic systems include a magnetic resonance imaging (MRI) system 1014, a computed tomography (CT) system 1016, and an ultrasound imaging system 1018. The diagnostic systems may be positioned in a single location or facility, such as a medical facility 1020, or may be remote from one another as shown in the case of ultrasound system 1018. The diagnostic systems are serviced from a centralized service facility 1022. Moreover, a plurality of field service units 1024 may be coupled in the service system for transmitting service requests, verifying service status, transmitting service data and so forth as described more fully below.

In the exemplary embodiment of FIG. 11, several different system modalities are provided with remote service by the service facility. Remote services include but are not limited to services, such as, remote monitoring, remote system control, immediate file access from remote locations, remote file storage and archiving, remote resource pooling, remote recording, and remote high speed computations. Remote services are provided to a particular modality depending upon the capabilities of the service facility, the types of diagnostic systems subscribing to service contracts with the facility, as well as other factors. In general, however, the present embodiment is particularly well suited to providing remote service to a wide variety of medical diagnostic system modalities, including MRI systems, CT systems, ultrasound systems, positron emission tomography (PET) systems, nuclear medicine systems, and so forth. Moreover, the various modality systems serviced in accordance with the present techniques may be of different type, manufacture, and model.

Depending upon the modality of the systems, various subcomponents or subsystems will be included. In the case of MRI system 1014, such systems will generally include a scanner, a control and signal detection circuit, a system controller, and an operator station. MRI system 1014 includes a uniform platform for interactively exchanging service requests, messages and data with service facility 1022 as described more fully below. MRI system 1014 is linked to a communications module 1032, which may be included in a single or separate physical package from MRI system 1014. In a typical system, additional components may be included in system 1014, such as a printer or photographic system for producing reconstructed images based upon data collected from the scanner.

Similarly, CT system 1016 will typically include a scanner, a signal acquisition unit, and a system controller. The scanner detects portions of x-ray radiation directed through a subject of interest. The controller includes circuitry for commanding operation of the scanner and for processing and reconstructing image data based upon the acquired signals. CT system 1016 is linked to a communications module 1048 for transmitting and receiving data for remote services. Moreover, like MRI system 1014, CT system 1016 will generally include a printer or similar device for outputting reconstructed images based upon data collected by the scanner.

In the case of ultrasound system 1018, such systems will generally include a scanner and data processing unit and a system controller. Ultrasound system 1018 is coupled to a communications module 1062 for transmitting service requests, messages and data between ultrasound system 1018 and service facility 1022.

Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics.

Where more than one medical diagnostic system is provided in a single facility or location, as indicated in the case of MRI and CT systems 1014 and 1016 in FIG. 11, these may be coupled to a management station 1070, such as in a radiology department of a hospital or clinic. The management station may be linked directly to controllers for the various diagnostic systems. The management system may include a computer workstation or personal computer 1072 coupled to the system controllers in an intranet configuration, in a file sharing configuration, a client/server arrangement, or in any other suitable manner. Moreover, management station 1070 will typically include a monitor 1074 for viewing system operational parameters, analyzing system utilization, and exchanging service requests and data between the facility 1020 and the service facility 1022. Input devices, such as a standard computer keyboard 1076 and mouse 1078, may also be provided to facilitate the user interface.

It should be noted that, alternatively, the management system, or other diagnostic system components, may be "stand-alone" or not coupled directly to a diagnostic system. In such cases, the service platform described herein, and some or all of the service functionality nevertheless be provided on the management system. Similarly, in certain applications, a diagnostic system may consist of a stand-alone or networked picture archiving communications and retrieval system or a viewing station provided with some or all of the functionality described herein.

The communication modules mentioned above, as well as workstation 1072 and field service units 1024 may be linked to service facility 1022 via a remote access network 1080. For this purpose, any suitable network connection may be employed. Presently preferred network configurations include both proprietary or dedicated networks, as well as open networks, such as the Internet. Data may be exchanged between the diagnostic systems, field service units, and remote service facility 1022 in any suitable format, such as in accordance with the Internet Protocol (IP), the Transmission Control Protocol (TCP), or other known protocols. Moreover, certain of the data may be transmitted or formatted via markup languages such as the HyperText Markup Language (HTML), or other standard languages. The presently preferred interface structures and communications components are described in greater detail below.

Within service facility 1022, messages, service requests and data are received by communication components as indicated generally at reference numeral 1082. Components 1082 transmit the service data to a service center processing system, represented generally at reference numeral 1084 in FIG. 11. The processing system manages the receipt, handling and transmission of service data to and from the service facility. In general, processing system 1084 may include one or a plurality of computers, as well as dedicated hardware or software servers for processing the various service requests and for receiving and transmitting the service data as described more fully below.

Service facility 1022 also includes a bank of operator workstations 1086 which may be staffed by personnel who address the service requests and provide off and on-line service to the diagnostic systems in response to the service requests. Also, processing system 1084 may be linked to a system of databases or other processing systems 1088 at or remote from the service facility 1022. Such databases and processing systems may include extensive database information on operating parameters, service histories, and so forth, both for particular subscribing scanners, as well as for extended populations of diagnostic equipment.

Figure 12:
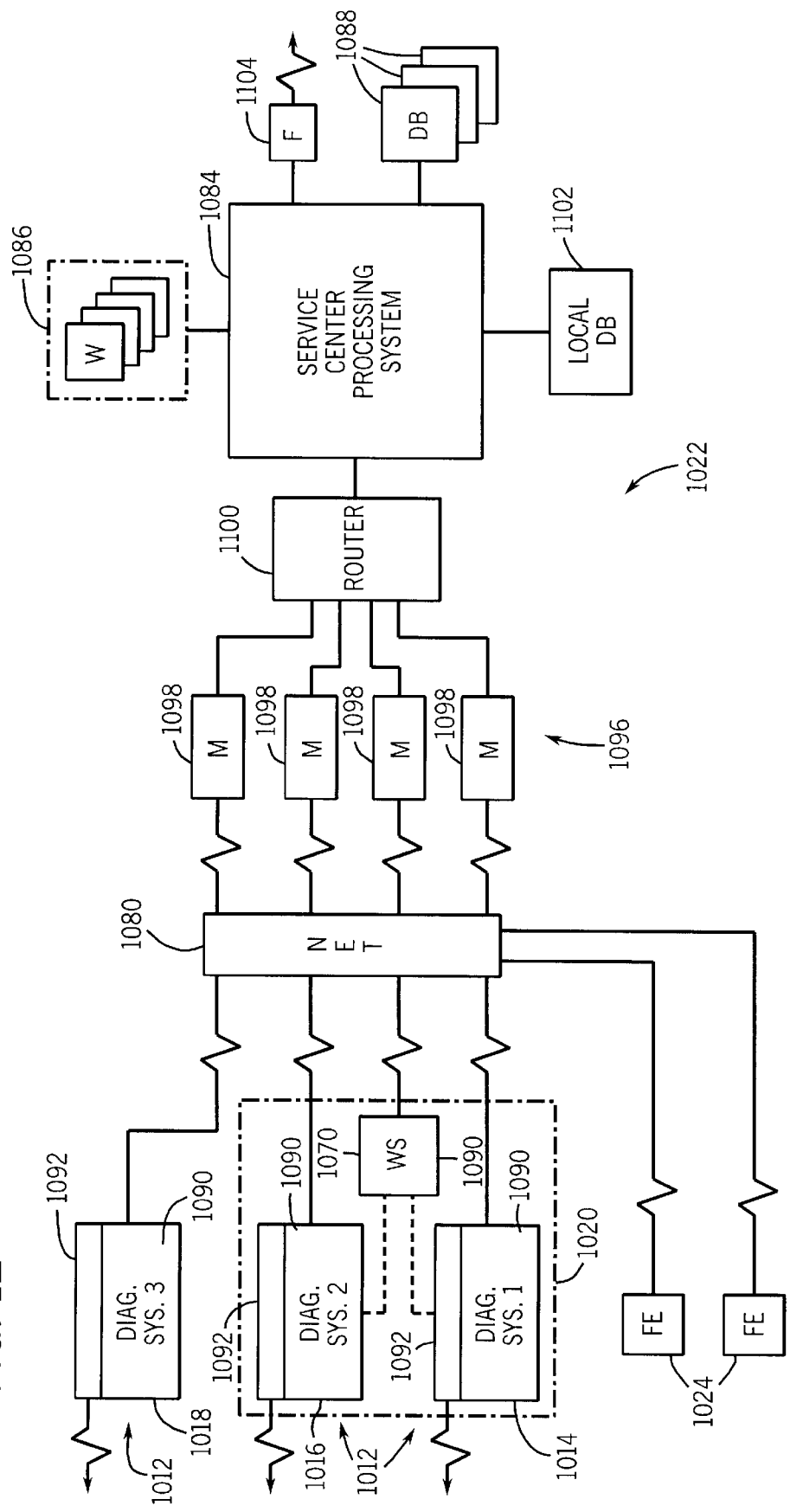
FIG. 12 is a block diagram of the systems shown in FIG. 11 illustrating certain functional components of the diagnostic systems and the service facility.

FIG. 12 is a block diagram illustrating the foregoing system components in a functional view. As shown in FIG. 12, the field service units 1024 and the diagnostic systems 1012 can be linked to the service facility 1022 via a network connection as illustrated generally at reference numeral 1080. Within each diagnostic system 1012, a uniform service platform 1090 is provided.

Platform 1090, which is described in greater detail below with particular reference to FIG. 13, includes hardware, firmware, and software components adapted for composing service requests, transmitting and receiving service data, establishing network connections and managing financial or subscriber arrangements between diagnostic systems and the service facility. Moreover, the platforms provide a uniform graphical user interface at each diagnostic system, which can be adapted to various system modalities to facilitate interaction of clinicians and radiologists with the various diagnostic systems for service functions. The platforms enable the scanner designer to interface directly with the control circuitry of the individual scanners, as well as with memory devices at the scanners, to access image, log and similar files needed for rendering requested or subscribed services. Where a management station 1070 is provided, a similar uniform platform is preferably loaded on the management station to facilitate direct interfacing between the management station and the service facility. In addition to the uniform service platform 1090, each diagnostic system is preferably provided with an alternative communications module 1092, such as a facsimile transmission module for sending and receiving facsimile messages between the scanner and remote service facilities.

Messages and data transmitted between the diagnostic systems and the service facility traverse a security barrier or "firewall" contained within processing system 1084 as discussed below, which prevents unauthorized access to the service facility in a manner generally known in the art. A modem rack 1096, including a series of modems 1098, receives the incoming data, and transmits outgoing data through a router 1100 which manages data traffic between the modems and the service center processing system 1084.

In the diagram of FIG. 12, operator workstations 1086 are coupled to the processing system, as are remote databases or computers 1088. In addition, at least one local service database 1102 is provided for verifying license and contract arrangements, storing service record files, log files, and so forth. Moreover, one or more communication modules 1104 are linked to processing system 1084 to send and receive facsimile transmissions between the service facility and the diagnostic systems or field service units.

Figure 13:
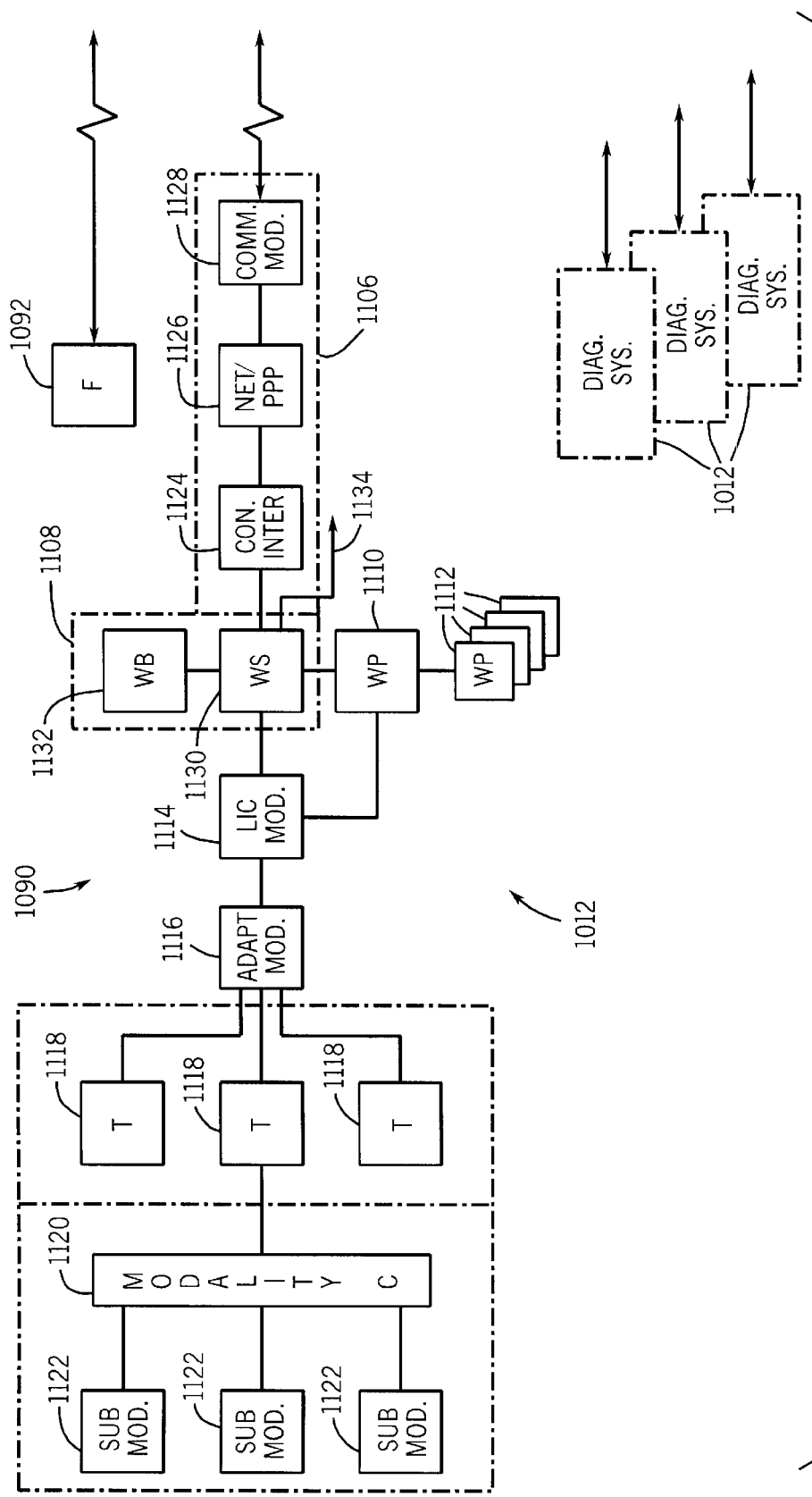
FIG. 13 is a block diagram of certain functional components within a diagnostic system of the type shown in FIG. 11 and FIG. 12 for facilitating interactive remote servicing of the diagnostic system.

FIG. 13 illustrates diagrammatically the various functional components comprising the uniform service platform 1090 within each diagnostic system 1012. As shown in FIG. 13, the uniform platform includes a device connectivity module 1106, as well as a network connectivity module 1108. Network connectivity module 1108 accesses a main web page 1110 which, as mentioned above, is preferably a markup language page, such as an HTML page displayed for the system user on a monitor at the diagnostic system. Main web page 1110 is preferably accessible from a normal operating page in which the user will configure examination requests, view the results of examinations, and so forth such as via an on-screen icon. Through main web page 1110, a series of additional web pages 1112 are accessible. Such web pages permit remote service requests to be composed and transmitted to the remote service facility, and facilitate the exchange of other messages, reports, software, protocols, and so forth as described more fully below.

It should be noted that as used herein the term "page" includes a user interface screen or similar arrangement which can be viewed by a user of the diagnostic system, such as screens providing graphical or textual representations of data, messages, reports and so forth. Moreover, such pages may be defined by a markup language or a programming language such as Java, per, java script, or any other suitable language.

Network connectivity module 1108 is coupled to a license module 1114 for verifying the status of license, fee or contractual subscriptions between the diagnostic system and the service facility. As used herein, the term "subscription" should be understood to include various arrangements, contractual, commercial or otherwise for the provision of services, information, software, and the like, both accompanies with or without payment of a fee. Moreover, the particular arrangements manages by systems as described below may include several different types of subscriptions, including time-expiring arrangements, one-time fee arrangements, and so-called "pay per use" arrangements, to mention but a few.

License module 1114 is, in turn, coupled to one or more adapter utilities 1116 for interfacing the browser, server, and communications components with modality interface tools 1118. In a presently preferred configuration, several such interface tools are provided for exchanging data between the system scanner and the service platform. For example, modality interface tools 1118 may include applets or servlets for building modality-specific applications, as well as configuration templates, graphical user interface customization code, and so forth. Adapters 1116 may interact with such components, or directly with a modality controller 1120 which is coupled to modality-specific subcomponents 1122.

The modality controller 1120 and modality-specific subcomponents 1122 will typically include a preconfigured processor or computer for executing examinations, and memory circuitry for storing image data files, log files, error files, and so forth. Adapter 1116 may interface with such circuitry to convert the stored data to and from desired protocols, such as between the HyperText Transfer Protocol (HTTP) and DICOM, a medical imaging standard for data presentation. Moreover, transfer of files and data as described below may be performed via any suitable protocol, such as a file transfer protocol (FTP) or other network protocol.

In the illustrated embodiment, device connectivity module 1106 includes several components for providing data exchange between the diagnostic system and the remote service facility. In particular, a connectivity service module 1124 provides for interfacing with network connectivity module 1108. A Point-to-Point Protocol (PPP) module 1126 is also provided for transmitting Internet Protocol (IP) packets over remote communication connections. Finally, a modem 1128 is provided for receiving and transmitting data between the diagnostic system and the remote service facility. As will be appreciated by those skilled in the art, various other network protocols and components may be employed within device connectivity module 1106 for facilitating such data exchange.

Network connectivity module 1108 preferably includes a server 1130 and a browser 1132. Server 1130 facilitates data exchange between the diagnostic system and the service facility, and permits a series of web pages 1110 and 1112 to be viewed via browser 1132. In a presently preferred embodiment, server 1130 and browser 1132 support HTTP applications and the browser supports java applications. Other servers and browsers, or similar software packages may, of course, be employed for exchanging data, service requests, messages, and software between the diagnostic system, the operator and the remote service facility. Finally, a direct network connection 1134 may be provided between server 1130 and an operator workstation, such as management station 1070 within the medical facility (see FIGS. 11 and 12).

In a present embodiment, the components comprising network connectivity module may be configured via an application stored as part of the uniform platform. In particular, a Java application licensed to a service engineer enables the engineer to configure the device connectivity at the diagnostic system to permit it to connect with the service facility.

Figure 14:
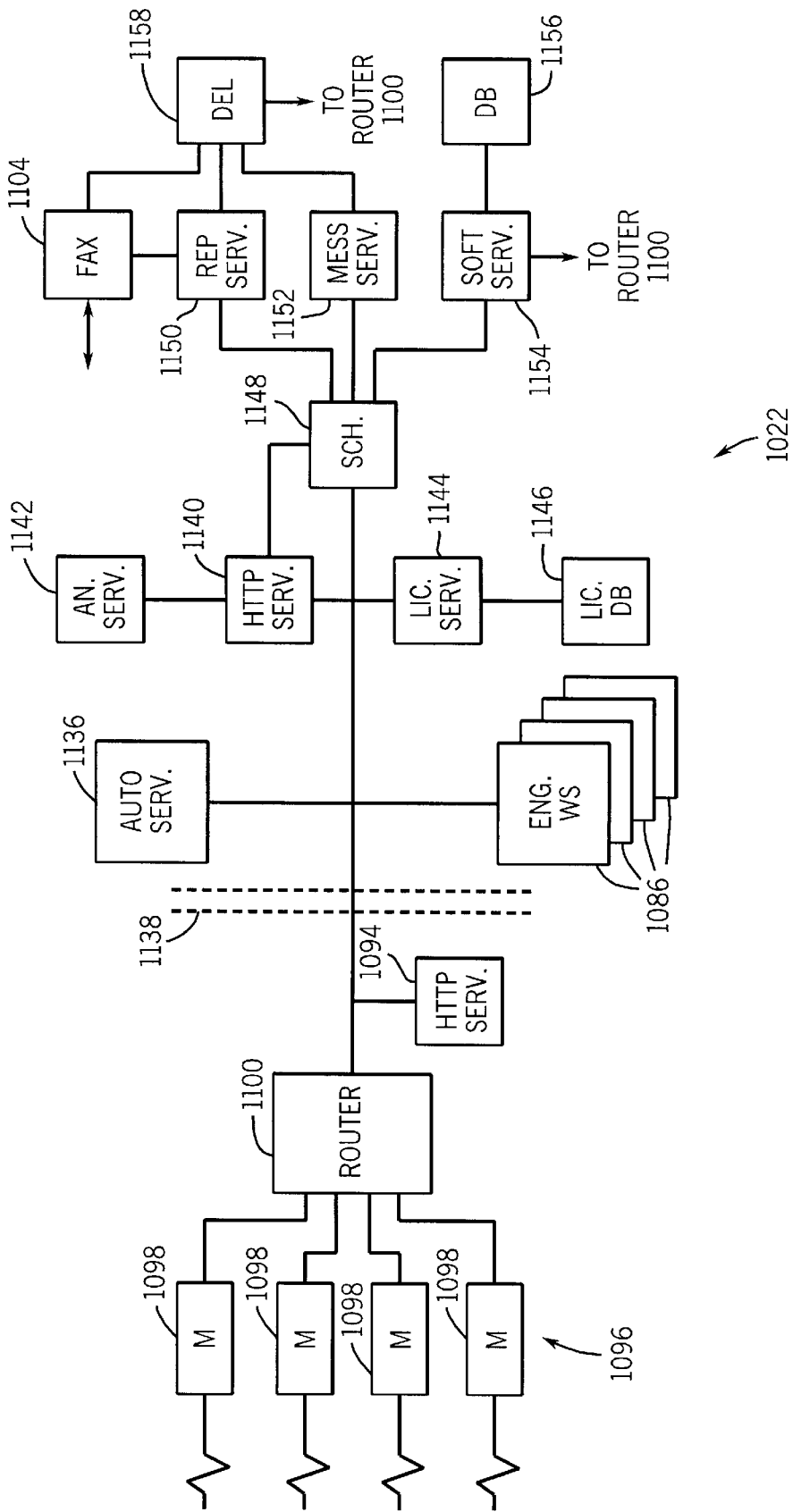
FIG. 14 is a block diagram of certain of the functional components of the service facility illustrated in FIGS. 11 and 12 for rendering interactive remote service to a plurality of medical diagnostic systems.

FIG. 14 illustrates exemplary functional components for service facility 1022. As indicated above, service facility 1022 includes a modem rack 1096 comprising a plurality of modems 1098 coupled to a router 1100 for coordinating data communications with the service facility. An HTTP service server 1094 receives and directs incoming and outgoing transactions with the facility. Server 1094 is coupled to the other components of the facility through a firewall 1138 for system security. Operator workstations 1086 are coupled to the port manager for handling service requests and transmitting messages and reports in response to such requests.

An automated service unit 1136 may also be included in the service facility for automatically responding to certain service requests, sweeping subscribing diagnostic systems for operational parameter data, and so forth, as described below. In a presently preferred embodiment, the automated service unit may operate independently of or in conjunction with the interactive service components comprising processing system 1084. It should be noted that other network or communications schemes may be provided for enabling the service facility to communicate and exchange data and messages with diagnostic systems and remote service units, such as systems including outside Internet service providers (ISP's), virtual private networks (VPN's) and so forth.

Behind firewall 1138, an HTTP application server 1140 coordinates handling of service requests, messaging, reporting, software transfers and so forth. Other servers may be coupled to HTTP server 1140, such as service analysis servers 1142 configured to address specific types of service requests, as described more fully below. In the illustrated embodiment, processing system 1084 also includes a license server 1144 which is coupled to a license database 1146 for storing, updating and verifying the status of diagnostic system service subscriptions. Alternatively, where desired, license server 1144 may be placed outside of fire wall 1138 to verify subscription status prior to admission to the service facility.

Handling of service requests, messaging, and reporting is further coordinated by a scheduler module 1148 coupled to HTTP server 1140. Scheduler module 1148 coordinates activities of other servers comprising the processing system, such as a report server 1150, a message server 1152, and a software download server 1154. As will be appreciated by those skilled in the art, servers 1150, 1152 and 1154 are coupled to memory devices (not shown) for storing data such as addresses, log files, message and report files, applications software, and so forth. In particular, as illustrated in FIG. 14, software server 1154 is coupled via one or more data channels to a storage device 1156 for containing transmittable software packages which may be sent directly to the diagnostic systems, accessed by the diagnostic systems, or supplied on pay-per-use or purchase basis. Message and report servers 1152 and 1150 are further coupled, along with communications module 1104, to a delivery handling module 1158, which is configured to receive outgoing messages, insure proper connectivity with diagnostic systems, and coordinate transmission of the messages.

In a presently preferred embodiment, the foregoing functional circuitry may be configured as hardware, firmware, or software on any appropriate computer platform. For example, the functional circuitry of the diagnostic systems may be programmed as appropriate code in a personnel computer or workstation either incorporated entirely in or added to the system scanner. The functional circuitry of the service facility may include additional personal computers or workstations, in addition to a main frame computer in which one or more of the servers, the scheduler, and so forth, are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of remote service data between the diagnostic systems and a remote service facility, which is preferably implemented in an interactive manner to provide regular updates to the diagnostic systems of service activities.

As described above, both the diagnostic systems and the field service units preferably facilitate interfacing between a variety of diagnostic system modalities and the remote service facility via a series of interactive user-viewable pages. Exemplary pages include capabilities of providing interactive information, composing service requests, selecting and transferring messages, reports and diagnostic system software, and so forth. Pages facilitate the interaction and use of remote services, such as, remote monitoring, remote system control, immediate file access from remote locations, remote file storage and archiving, remote resource pooling, remote recording, and remote high speed computations.

The user can access specific documents described in text areas of the pages by selection of all or a portion of the text describing the documents. In the presently preferred embodiment, the accessed documents may be stored in local memory devices within the diagnostic system, or selection of the text may result in loading of a uniform resource locator (URL) for accessing a remote computer or server via a network link.

Advantageously, service system 1010 (FIG. 11) incorporating the MR system described with reference to FIG. 1 provides remote services, such as, remote control, remote monitoring, remote storage, remote resource pooling, remote diagnostics, and remote accessing. As such, service system 1010 may provide imaging systems with upgrades in software to operate the imaging device or the interface, service diagnosis for maintenance and repair of the imaging device or the interface, management of contractual subscriptions between the imaging device and the remote facility, and confirmation of images with images stored from prior sessions. Technologists particularly benefit from the remote services provided. Technologists can control the imaging device remotely, access information remotely, and store information remotely. In this manner, for example, technologists have scheduling tables and information more readily available.

While the embodiments illustrated in the Figures and described above are presently preferred, it should be understood that the embodiments are offered by way of example only. Other embodiments may include enhanced remote services and features made possible by the structures and functionality described above. The invention is not limited to a particular embodiment, but extends to various modifications, combinations, and permutations that nevertheless fall within the scope and spirit of the appended claims.

What is claimed is:

1. A medical image data acquisition and manipulation system coupled to a network, the network coupling medical imaging devices of at least first and second different medical image data acquisition modalities, each medical image data acquisition modality including functions which are common to each of the first and second medical image data acquisition modalities, the system comprising:

a medical image acquisition imaging device;

a network coupling the imaging device to a remote facility, wherein the network provides the imaging device with remote services from the remote facility;

an interface associated with the imaging device, the interface comprising a display and a programmed data processor for providing a uniform interface image on the display despite the specific data acquisition modality of the at least first and second modalities, the uniform interface image comprising:

a function navigation space including function icons corresponding to procedures which are common to both the first and second data acquisition modalities; and a workspace adjacent the function navigation space for displaying, analyzing and manipulating images of a type consistent with the specific data acquisition modality; and a pointing device for moving a pointer icon about the display and for selecting displayed icons;

wherein, when an icon is selected, the processor correlates the selected icon with a corresponding command and executes the command, each procedure which is common to the first and second modalities includes procedure specific subprocesses and wherein the workspace includes a workflow navigation space in which, when a function icon is selected, the processor displays a workflow icon set including a separate workflow icon corresponding to each subprocess of the process associated with the selected function icon and for the specific modality, each subprocess includes subprocess specific parameters, the workspace includes both an imaging window and a parameter setting space adjacent the imaging window and, when a workflow icon is selected, the processor displays a parameter value set and setting icons in the setting space which correspond to the subprocess specific parameters associated with the selected workflow icon, each parameter value indicating the current parameter value, the setting icons useable to modify the current parameter values and wherein a plurality of physicians may prescribe imaging using the specific modality and each physician may have different initial current parameter value settings for each subprocess, the processor storing a table which correlates each physician with physician specific initial current parameter value settings, a physician identifier provided to the processor and, when a specific workflow icon is selected, the processor accesses the table, correlates the physician identifier with the selected subprocess initial current parameter value settings and provides parameter icons indicating the initial current parameter value settings.

2. The imaging system of claim 1, wherein the remote services comprise upgrades in software to operate any one of the medical imaging device and the interface.

3. The imaging system of claim 1, wherein the remote services comprise service diagnosis for maintenance and repair of any one of the imaging device and the interface.

4. The imaging system of claim 1, wherein the remote services comprise remote control of the image device by an operator located at a different location than the medical imaging device.

5. The imaging system of claim 1, wherein the remote services comprise management of contractual subscriptions between the imaging device and the remote facility.

6. The imaging system of claim 1, wherein the remote services comprise remote storage of images and data from the imaging device.

7. The imaging system of claim 1, wherein the remote services comprise remote access to images and data from the imaging device.

8. The imaging system of claim 7, wherein the data comprises scheduling tables and information useable by operators of the imaging device.

9. The imaging system of claim 1, wherein the remote services comprise confirmation of images with images stored from prior sessions.

10. The imaging system of claim 1, wherein the subprocesses of each procedure typically are performed in an exemplary workflow pattern including a series of consecutive steps and the workflow icons are arranged in an order of the exemplary workflow pattern.

11. The imaging system of claim 1, wherein the workflow icons include a setup icon which corresponds to the process of positioning a patient for imaging, when the setup icon is selected, the processor providing a position window in the workspace and providing an image of a properly positioned patient in the position window.

12. The imaging system of claim 1, wherein subprocess parameters corresponding to each subprocess include a commonly modified parameter subset and a seldom modified parameter subset and wherein, when a workflow icon is selected the processor displays parameter values and setting icons which correspond to the commonly modified parameter subset and a toolbox icon, when the toolbox icon is selected, the processor opening the toolbox window and displaying the parameter values and setting icons which correspond to the seldom modified parameter set.

13. The imaging system of claim 1, wherein the processor stores a workflow table which correlates subprocess sets with each modality function and wherein the processor provides a protocols icon which, when selected, causes the processor to display icons in the workspace for modifying the subprocess set to provide a modified subprocess set which is then stored by the processor as the subprocess set, the next time the corresponding function icon is selected, the processor providing a workflow icon for each of the subprocesses in the subprocess set.

14. The imaging system of claim 1, wherein a plurality of physicians may prescribe imaging using the specific data acquisition modality and each physician may have a different subprocess procedure for data acquisition modality functions, the processor storing a table which correlates each physician with a physician specific subprocess set for each function, a physician identifier provided to the processor and, when a specific function icon is selected, the processor accesses the table, correlates the physician identifier with selected function subprocess set and provides a workflow icon for each subprocess in the subprocess set.

15. The imaging system of claim 1, for use with a plurality of modalities including radiography, fluoroscopy, angiography, magnetic resonance imaging, ultrasound, nuclear medicine imaging and computer tomography, wherein the processor provides a uniform interface image on the display despite the specific modality.

16. The imaging system of claim 1, wherein, in addition to the navigation space and the workspace, the processor also provides a domain space and a schedule icon in the domain space and wherein, when the schedule icon is selected, the processor dears the workspace and navigation space and therein provides a schedule metaphor image which includes imaging system scheduling information.

17. The imaging system of claim 1, wherein, in addition to the navigation space and the workspace, the processor also provides a domain space and a logbook icon in the domain space and wherein, when the logbook icon is selected, the processor clears the workspace and navigation space and therein provides a logbook metaphor image which includes imaging system logbook information.

* * * * *